(12) United States Patent
Beshay et al.

(10) Patent No.: US 11,255,794 B1
(45) Date of Patent: Feb. 22, 2022

(54) MULTI-SUBSTRATE PASSIVE COLORIMETRIC SENSORS FOR DETECTING TOXIC INDUSTRIAL CHEMICALS AND CHEMICAL WARFARE AGENTS

(71) Applicant: INTELLIGENT OPTICAL SYSTEMS, INC., Torrance, CA (US)

(72) Inventors: Manal Beshay, Rancho Palos Verdes, CA (US); Janet L. Jensen, Aberdeen, MD (US); James M. Cress, Aberdeen, MD (US)

(73) Assignees: Intelligent Optical Systems, Inc., Torrance, CA (US); United States of America as Represented by the Secretary of the Army, Washington, DC (US)

( * ) Notice: Subject to any disclaimer, the term of this patent is extended or adjusted under 35 U.S.C. 154(b) by 213 days.

(21) Appl. No.: 16/283,712

(22) Filed: Feb. 22, 2019

Related U.S. Application Data

(60) Provisional application No. 62/643,137, filed on Mar. 14, 2018, provisional application No. 62/633,619, filed on Feb. 22, 2018.

(51) Int. Cl.
*G01N 21/78* (2006.01)
*G01N 33/00* (2006.01)
*G01N 21/77* (2006.01)

(52) U.S. Cl.
CPC ....... *G01N 21/783* (2013.01); *G01N 33/0057* (2013.01); *G01N 2021/7756* (2013.01); *G01N 2021/7759* (2013.01)

(58) Field of Classification Search
CPC ....... G01N 33/0057; G01N 2021/7756; G01N 2021/7759; G01N 21/783; G01N 33/528; G01N 33/52; G01N 21/8483
See application file for complete search history.

(56) References Cited

U.S. PATENT DOCUMENTS 5,153,520 A   10/1992  Dumbeck
6,435,003 B1   8/2002  Warburton
(Continued)

OTHER PUBLICATIONS

George M. Murray, "Detection & Screening of Chemicals related to the Chemical Weapons Convention", This article was published in the Encyclopedia of Analytical Chemistry in 2013 by John Wiley & Sons, Ltd.
(Continued)

*Primary Examiner* — Rebecca M Fritchman
(74) *Attorney, Agent, or Firm* — Brian Billett

(57) ABSTRACT

Disclosed are systems and methods for the robust passive detection of airborne toxins using a colorimetric sensor coating onto a optically transparent substrate. In certain embodiments, the substrate is affixed to an adhesive material (tape). In certain embodiments, the sensor and substrate are transparent. In various embodiments, multiple sensors are coated onto selected substrate for the simultaneous detection of multiple toxins. In various embodiments, the sensed or detected toxins include a number of chemical warfare agents and toxic industrial chemicals. In various implementations, the tape is affixed to a remote surface, which may be visually monitored by a camera directly by focusing the camera on the tape or may be affixed to a camera lens by an adhesive backing, such that colorimetric sensor changes may be observed through the lens itself. Sensor claddings consist of optical grade polymers immobilized with colorimetric and/ or fluorescent indicators that undergo optical changes upon exposure to their target analyte. Typical substrate cross-linked polymers are urethane acrylate polymer based, co-polymerized with silicone backbone such as dimethyl siloxane, which in general is chemically inert, yet leaves the polymer with the large free-volume necessary for rapid target diffusion. The polymer is cured after immobilization
(Continued)

with target indicator mixture, and simultaneously cross-linked by UV light or heat.

21 Claims, 35 Drawing Sheets
(24 of 35 Drawing Sheet(s) Filed in Color)

(56) References Cited

U.S. PATENT DOCUMENTS

| | | | |
|---|---|---|---|
| 6,947,138 B2 * | 9/2005 | Arno | G01N 21/78 |
| | | | 356/437 |
| 7,487,662 B2 | 2/2009 | Schabron et al. | |
| 7,514,039 B2 | 4/2009 | Loomis | |
| 8,409,525 B1 * | 4/2013 | Farmer | G01T 1/2008 |
| | | | 422/403 |
| 2004/0038385 A1 | 2/2004 | Langlois et al. | |
| 2007/0243107 A1 | 10/2007 | Chase et al. | |
| 2016/0298450 A1 | 10/2016 | Mcalary et al. | |
| 2017/0067825 A1 | 3/2017 | Sato et al. | |
| 2017/0292068 A1 * | 10/2017 | Kandapallil | C09K 9/02 |

OTHER PUBLICATIONS

Beshay, Manal et al., "Recent advances towards a fiber optic sensor for nerve agent", Chemical, Biological, Radiological, Nuclear, and Explosives (CBRNEJ Sensing IX), Proc. of SPIE, 2008.

* cited by examiner

| Condition | Temperature (°C) | %RH |
|---|---|---|
| 1 | 30 | 25 |
| 2 | 30 | 50 |
| 3 | 30 | 75 |
| 4 | 20 | 50 |
| 5 | 40 | 50 |
| 6 | 0 | 5 |
| 7 | 0 | 87 |
| 8 | 50 | 5 |
| 9 | 50 | 87 |

| Agent | Low Concentration (mg/m$^3$) | High Concentration (mg/m$^3$) |
|---|---|---|
| GB | 0.01 | 10 |
| GD | 0.01 | 10 |
| HD | 0.50 | 20 |
| VX* | 0.01 | 1.0 |

| GD Concentration | | GB Concentration | |
|---|---|---|---|
| ppm | mg/m$^3$ | ppm | mg/m$^3$ |
| 2 | 14.9 | 2 | 11.5 |
| 10 | 75.5 | 10 | 57.3 |
| 20 | 149 | 20 | 114 |

| | Parameter | Target Values | Obtained Values |
|---|---|---|---|
| Sensor Response Specifications | Measurement Range | 1-100 ppm | GB/GD & GA: 1-100 ppm<br>CG: 1- 25 ppm |
| | Response Time<br>Alarm:<br>Measurement T$_{95}$: | <20 seconds<br>< 1 minute | 30 seconds<br>2 minutes to T$_{95}$ |
| | Accuracy (+/-) | 1 ppm (0 to 10 ppm)<br>5 ppm (10 to 100 ppm) | 3 ppm (0 to 15 ppm)<br>7 ppm (15 to 100 ppm) |
| | Operational range T°C | -10 to +55 (with compensation) | 0 - 50 |
| | RH% | 5-95 (with compensation) | 5-95 (with compensation) |
| General System Specifications | Weight | <1 lb. | 188 grams (no USB cable), so ~0.5 lbs. |
| | Dimensions | ≤ 3" x 5" x 2" | L x W = 3.5" x 4" (not including cable coming out)<br>Height is 1.5", with tubes ~3.5" |
| | Detection State | Vapor | Vapor |
| | Power | DC or rechargeable battery powered | DC/USB power |
| | Battery Life | >10 hours of continuous operation | No battery attached. If used with Bluetooth, can test to see if it drains the battery out at the usage rate.<br><br>Maybe it could reach it, provided battery is large enough, but if we put a sniffer, that will impact battery life. |
| | Serial Connection | USB 2.0, RS 232 | Currently Bluetooth 4.0. Change to USB will require major firmware rewrite, or can simply switch to a different controller. |
| | Enclosure | Potentially anodized aluminum | Currently 3D printed material, but can be made of anodized aluminum |
| | Input Voltage | 5 VDC 10 W | USB power, which is 5 VDC, and maximum of 10 W. |
| | Product Life | >5 years with calibration | |

Fig. 12

| Property | Polymer | | | | |
|---|---|---|---|---|---|
| | Raymat 690-4 | Raymat 690-2 | Raymat 145-28 | Raymat 144-28-3 | Raymat 1445 |
| Backbone Material | UV-urethane/ acrylate | UV-urethane/ acrylate | UV-silicone/ acrylate | UV-silicone/ acrylate | UV-silicone/ acrylate |
| Tensile Strength (MPa) | 0.70 | 0.72 | 0.89 | 0.97 | 0.94 |
| Elongation Break (%) | 15 | 16 | 18 | 24 | 23 |
| Oligomer/Monomer Mwt. | 6000/3000 | 6000/300 | 3000 | 6000/2000 | 6000 |
| Monomer Functionality %(w/w oligomer) | Di (11%) | Tri/mono (9%/2%) | Di (11%) | Di (11%) | Tri (11%) |
| Refractive Index (n) | 1.442 | 1.4473 | 1.45 | 1.4432 | 1.445 |

| | Polymer A | Polymer B | Polymer C | Polymer D | Polymer E | Polymer F | Polymer G | Polymer H | Polymer J | Polymer K | Polymer L |
|---|---|---|---|---|---|---|---|---|---|---|---|
| Manufacturer ID | | 1445 | | 145-2B | | 144-28-3 | 690-2 | | 690-4 | | |
| Modulus at 2.5% elongation (Mpa) | 11.43 | | | | 7.65 | 4.28 | 4.85 | 6.4 | | | |
| Tensile Strength (Mpa) | 2.13 | | | | 1.42 | 0.97 | 0.72 | 1.14 | | | |
| Elongation at break (%) | 21 | | | | 21 | 24 | 16 | 19 | | | |
| mw oligomer | 2000 (84%) | 3000 (100%) | 3000 | 6000 | 6000/2000 (42%/42%) | 6000/2000 (42%/42%) | 6000/3000 (42%/42%) | 6000/3000 (32%/52%) | 6000/3000 (11%) | 2500 | 2500 |
| monomer | n/a | F-di (11%) | mono | tri | tri/mono (9%/2%) | F-di (11%) | tri/mono (9%/2%) | tri/mono (9%/2%) | F-di (11%) | di | mono |
| viscosity (cps) | 6547 | 6125 | 5340 | 6000 | 5764 | 4107 | 5609 | 5513 | 6280 | 2500 | 2200 |
| $n_1$ cured | 1.4604 | 1.45 | 1.446 | 1.442 | 1.4512 | 1.4432 | 1.4473 | 1.45 | 1.442 | 1.426 | 1.425 |
| Fiber doping level | | | | | 0.5 / 2.5 (3%) | 1.5 / 7.5 (9%) | 1.5 / 7.5 (9%) | 1.5 (6%) | | | |
| $n_1$ doped | | | | | 1.4553 | 1.4500 | 1.4540 | 1.4547 | | | |
| sensor fiber mean strength (lb/kpsi) strength (pure fiber) | | | | | 2.34 / 192 (100) 1.95 / 160 (100) | 1.62 / 133 (100) 2.26 / 119 (125) 1.83 / 150 (100) | 1.43 / 117 (100) 2.28 / 120 (125) 1.63 / 134 (100) | 2.65 / 140 (125) 2.21 / 116 (125) | | | |
| 50 ppm HCN max signal, dB/m | | | | | 8 (100) @532nm | 8 (100) (125) @632nm | 7.5 (100) 5 (125) @632nm | | | | |
| Resp. time to 0.2 dB/m and T90 (@50ppm) | | | | | ~20/300+ (100) @532 | 15/360 (100) 10/110 (125) @632 | 4/60 (100) 4/60 (125) @632 | | | | |
| MFG. conditions | | | | | 1 lamp 25% 25m/min 98% conc. (100) | 2 lamps 25% ea 13 m/min 92% (100) 93% (125) | 2 lamps 25% ea 13 m/min 90% (100) 96% (125) | 1 lamp 25% 13m/min 85% (125) | | | |
| Fiber characteristics | | | | | acceptable cyanide fiber, clear colored | good response (T90 more than 690-2), honey colored | excellent response, honey colored | honey colored | | | |

Primary coating: 1.0-2.0 Mpa (modulus), elongation > 80%
Secondary Coating: > 400 Mpa (modulus), elongation > 15%
Single Coating: 30-100 Mpa (modulus), elongation > 25%

Fig. 14B

| Detection Ticket | Agents Detected | Color after Reaction |
|---|---|---|
| Nerve agents | GA<br>GB/GD<br>VX | |
| Blister agents | HD<br>Lewisite<br>CX | |
| Blood agents | AC<br>CK | |
| Choking agents | CG/DP<br>Chlorine/Chloropicrin | |

| Experiment Number | Temperature, °C | Relative Humidity, % |
|---|---|---|
| 1 | 10 | 5 |
| 2 | 10 | 95 |
| 3 | 30 | 50 |
| 4 | 50 | 5 |
| 5 | 50 | 95 |

Fig. 25

Table 3-4    Target Chemical Vapor Detection Scheme for the Proposed MIKE-Tape Development

| Chemical Category | Target Agent | Measurement Range | Target Level of Detection |
|---|---|---|---|
| CWA | HD mustard (CEES) | 0-200 mg/m3 | Aerosol |
|  | Vx | 0-200 mg/m3 | Aerosol |
|  | GB/GD (DFP) | 0-200 mg/m3 | Aerosol |
| TICs | Hydrogen cyanide | 0-100 ppm | 5 ppm |
|  | Phosgene | 0-50 ppm | 5 ppm |
|  | Ammonia | 0-200 ppm | 5 ppm |
|  | Chlorine | 0-20 ppm | 5 ppm |

Fig. 26

| Target Analyte | PEL (mg/m³) | IDLH (mg/m³) | Range (mg/m³) |
|---|---|---|---|
| HCN | 11.05 | 55.27 | 5-100 |
| H₂S | 20 | 100 | 10-250 |
| Cl₂ | 2.8 | 29 | 1-50 |
| Sarin/Soman GB/GD | 100 | 0.1 | 1-250 |
| Cyanogen Chloride | 0.6 | 30 | 5-100 |
| Ammonia | 34.83 | 208.96 | 20-500 |
| Ethylene Oxide | 1.8 | 1441.41 | 10-2500 |
| Second HCN Channel | 11.05 | 55.27 | 5-100 |
| Second Cl₂ Channel | 2.9 | 29 | 1-100 |
| Strong Acid (HCl)* | 10 | 25 | 10-25 |
| Arsine | 0.2 | 9.54 | 1-50 |
| Formaldehyde | 0.92 | 24.58 | 2.5-100 |
| Phosgene | 0.4 | 8.09 | 1-50 |
| Reference Channel | NA | NA | NA |

MULTI-SUBSTRATE PASSIVE COLORIMETRIC SENSORS FOR DETECTING TOXIC INDUSTRIAL CHEMICALS AND CHEMICAL WARFARE AGENTS

RELATED APPLICATIONS

This application claims priority to U.S. provisional patent application 62/633,619 filed on Feb. 22, 2018, the entirety of which are incorporated herein. This application claims priority to U.S. provisional patent application 62/643,137, filed on Mar. 14, 2018, the entireties of which is incorporated herein. U.S. patent application Ser. No. 14/089,627, filed on Nov. 25, 2013, is incorporated herein in its entirety.

GOVERNMENT LICENSE RIGHTS

This invention was made with government support under contract #W911SR-18-0023 awarded by the Department of Defense. The government has certain rights in the invention.

FIELD OF THE INVENTION

The field of the disclosure relates to passive sensors for detecting toxic industrial chemicals and chemical warfare agents.

BACKGROUND

In conflict areas, military personnel are in constant danger from chemical and biological threat exposure, which has extended to civilian threats in recent terrorist attacks, emphasizing the critical need for advanced detection techniques. Unmanned Autonomous Systems (UAS) are ideal means of monitoring locations which may be hazardous or otherwise problematic for live manned operations.

During the Cold War era, the power to deploy weapons of mass destruction (WMD) was only available to a few nation-states with large economic, political, industrial, military, and social resources. The probability of an attack was considered low; both the U.S. and the Soviet Union subscribed to mutually assured destruction, a standoff paradigm whereby neither had the incentive to be the first to launch a WMD attack, since utter annihilation would befall both sides.

In the post-Cold-War era, the Soviet WMD stockpile has become dispersed, with more countries ramping up R&D and production, while scientific and technical knowhow has become more readily available. One of the greatest challenges to the safety of the United States is the threat posed by adversaries employing irregular, disruptive, and potentially catastrophic strategies—including the use of terror, asymmetric attacks, and WMD, to challenge, marginalize, erode, and paralyze U.S. power. In simple terms, even small bands of terrorists or lone wolves have the potential to inflict massive damage. Conventional measures of deterrence are obsolete against an elusive enemy with few tangible physical assets at risk and the willingness to die in the pursuit of a cause.

In response, the U.S. Department of Defense has developed a comprehensive Chemical and Biological Defense Program, whose mission is to enable warfighters to operate in all WMD environments unimpeded by chemical, biological, radiological, and nuclear effects. Research and development (R&D), technology acquisition, and fielding are entrusted to a single, cross-services chain of command: the Joint Program Executive Office for Chemical and Biological Defense (JPEO-CBD), which seeks to continuously improve the portfolio of technologies to address this ever-evolving threat. R&D of new capabilities can take years to accomplish, at a cost of millions to billions of dollars; therefore, rather than start from scratch, the JPEO-CBD sources innovations via interagency and industry relationships. The advantage of this approach is a basket of cheaper, faster, more effective new technologies. The downside is the lack of integration of disparate technologies taken case-by-case from the private sector. Therefore, multifunctionality and interoperability are desirable features of WMD abatement technologies. Most importantly, near-real or real-time detection is critical to ensuring proper coordination and response—and this is where advanced sensors play a crucial role. The goal is to move measurements from near real time (<15 minutes) to real time (~1 to 10 seconds) at the short-term exposure limit (STEL) or the immediately dangerous to life and health (IDLH) level, without significant loss of sensitivity or specificity.

The need for CBD sensing lies on a continuum ranging from extreme events, involving super-catastrophes such as a WMD breach of homeland defenses, to routine prevention of more moderate mishaps.

Toxic environmental threats include both chemical warfare agents ("CWA's"), and toxic industrial chemicals ("TIC's"). Although distribution and use has been generally limited to armed forces, colorimetric detection paper M8 and M9 has been available for the detection of a limited number of chemical warfare agents by personnel by directly exposing the detection paper to environments where airborne CWA's are suspected. M8 and M9 detection paper are unsuitable, however, for a variety of real-world scenarios and are generally used directly by personnel. Among other limitations, the paper is unstable in many real-world conditions, and is known for poor discrimination and frequent false positive indications.

A more advanced available technology than M8/M9 paper for sensing CWA's and TIC's may be available using a device known as an electronic nose. E-noses are devices capable of measuring and characterizing volatile aromas released from a multitude of sources. Electronic noses were originally used for quality control in the food, beverage, and cosmetics industries. Current applications include detection of hazardous chemicals and explosives, detection of odors specific to diseases for medical diagnosis, and detection of pollutants and gas leaks for environmental protection. These devices are complex and require power supplies as well as mechanical and electrical components. Additionally, passive integration with existing systems is not possible.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 6A shows the idealized test points. FIG. 6B shows the test points achievable in real-world conditions.

FIG. 12 show criteria and obtained specifications for an opto-electronic reader device for unmanned operation and use of MIKE-tape.

FIG. 13 shows a field use of a small hand-held UAS as an exemplar launch for utilizing MIKE-tape in a highly mobile configuration.

FIG. 14A-B show sets of polymers considered potentially suitable for MIKE-tape as a multi-sensor carrier [polymers A-L].

FIG. 25 shows experimental DOE matrix to determine temperature and humidity effects on sensitivity.

FIG. 26 shows the target chemical vapor detection scheme for the MIKE-Tape development.

FIG. 31A-C show images of a test implementation of MIKE-tape for detecting phosgene vapor.

DESCRIPTION

Disclosed are systems and methods for the robust passive detection of airborne toxins using a colorimetric sensor clad to a stable substrate. In certain embodiments, the substrate is affixed to an adhesive material (tape). In certain embodiments, the sensor and substrate are transparent. In various embodiments, multiple sensors are coating onto a substrate for the simultaneous detection of multiple toxins. In various embodiments, the sensed or detected toxins include a number of chemical warfare agents and toxic industrial chemicals, In various implementations, the tape is affixed to a remote surface, which may be visually monitored by a camera directly by focusing the camera on the tape or may be affixed to a camera lens by an adhesive backing, such that colorimetric sensor changes may be observed through the lens itself. The transparent substrate may also be adhesively affixed to windows for optical detection of sensed toxins on the outside surface of the window by a person or camera on the opposite, presumably protected side of the window. In an exemplar installation, the camera with a sensor affixed to its lens may be onboard an unmanned aerial System ("UAS") or unmanned ground Systems ("UGS"). An exemplar embodiment application is known as the Multi agent Indicator Kit and Equipment ("MIKE-Tape"). Certain aspects of the sensor substrate including additives which enhanced sensor capabilities is described.

The autonomous operation of UAS's and UGS's has been improving to a degree that a single pilot can fly or operate several drones at once. Adding functionality for chemical detection on short flight missions to locate contamination provides immediate intelligence, surveillance and reconnaissance capabilities.

Chemical detectors are commercially available for stand-off and typical monitoring applications. However the size, weight and power-consumption are important factors for real-world implementation. Moreover, mechanical, hardware and software integration complexity can limit the adaptability of technologies. Colorimetric detection such as in the disclosed system solves many of these problems, but itself may be highly dependent on the conditions of use to facilitate efficacy of the colorimetric sensor chemistry. In the disclosed methods, an effective modification of the sensor is provided to account for operating the sensor in very low humidity environmental conditions. Recent uses of toxic warfare agents have occurred in very low humidity environments, making this operational concern relevant to effectiveness.

Disclosed are methods for loading functionalized colorimetric indicators into customized polymers, and then coating these polymers onto robust substrates for specific applications. These disclosed methods for developing sensor coated substrates may be implemented for remote sensing by affixing an adhesive coated sensor substrate to the camera lens of an unmanned or remotely operated air or ground system.

Figure 1:
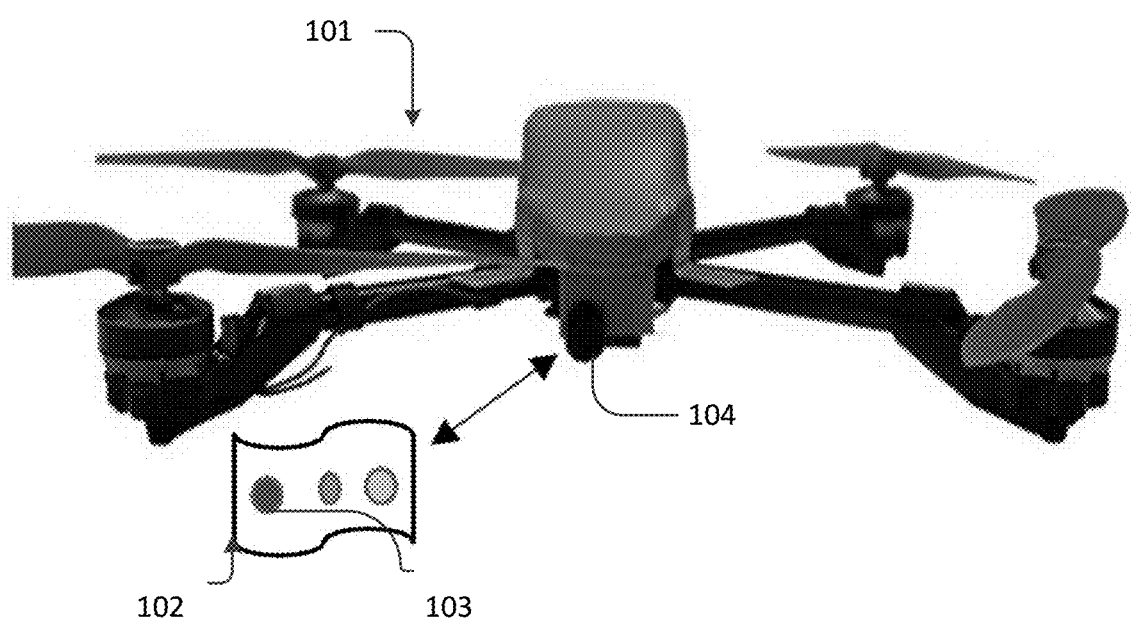
FIG. 1 depicts an exemplar embodiment of disclosed colorimetric sensors coating onto a transparent substrate and affixed to an unmanned aerial system camera.

FIG. 1 shows an application of the disclosed sensor 103 with adhesive backed transparent substrate 102 to the camera lens of a flying UAS 101 "eye" 104. Exemplar UAS's suitable for field operation implementation of a remote sensor application include the Black Hornet 2 nano PD100 or PD150. In this exemplar implementation, the sensor cladding 103 which is affixed to the camera by a transparent substrate 102 will detect any of several chemical warfare agents ("CWAs"), and toxic industrial chemicals ("TICs") in either aerosol or vapor phase, under a full range of real-world environmental conditions. Various embodiment sensor arrays will detect CWAs and generate a visual and self-reporting alarm via simple image processing of the passive sensor to operate for unmanned operation. This disclosure includes implementation embodiments which integrate, demonstrate, and validate the applicability of the Multi agent Indicator Kit and Equipment "MIKE-Tape" to UASs for field applications.

FIG. 1 also depicts an implementation embodiment of a flying copter camera and the integration Multi agent Indicator Kit and Equipment "MIKE-Tape." 102. An embodiment of polymer-based sensor claddings 103 are effective sensing coating materials for detecting live agents, showing high reactivity within <5 s response time. The shown multi-dot multi-agent sensor clad detection tape is suitable for passive integration, and requires no additional hardware, power, mechanical, data processing, electrical or optical processing structures other than those currently available onboard the system.

An objective was to develop a chemical warfare agent colorimetric detection platform that can improve the stability of M8 and M9 test papers, with added self-reporting and gas-phase detection capabilities. Improvement of the stability of current M8 test papers was accomplished by the application of polymer claddings to maximize their stability under adverse conditions. For some target agents, indicators are based on the detection of CWA hydrolysis by-products, through complex formation by an indicator dye-heavy metal chelating reaction, are incorporated in the sensor arrays to identify and quantify chemical warfare agent aerosols and vapors.

Figure 2:
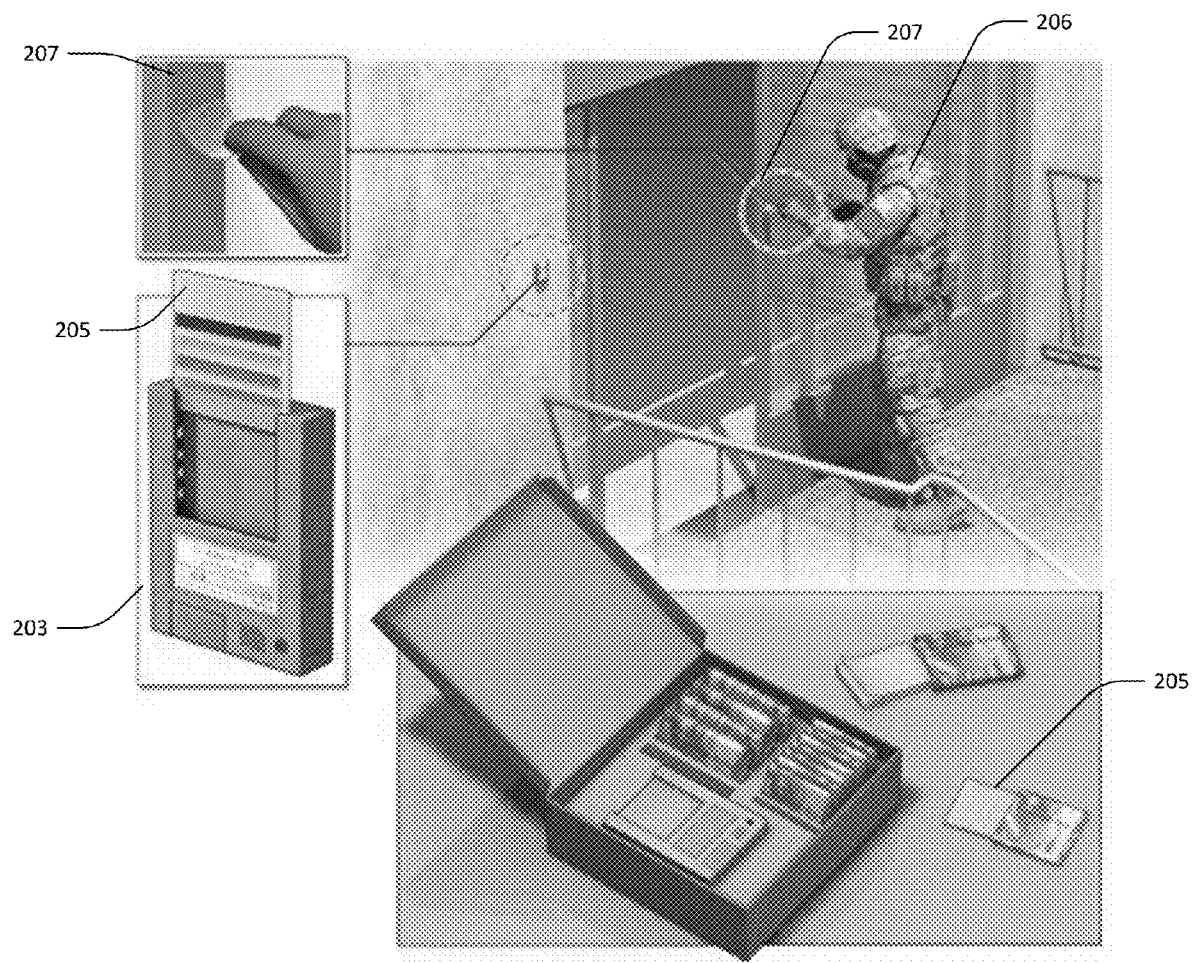
FIG. 2 shows an artist's rendering of an implementation of disclosed high-durability colorimetric sensors used in the field by military personnel and mounted for unmanned operation.

Another objective was to provide for unattended sensor array operation to meet the conditions of remote sensing. FIG. 2 shows an artist's depiction of an exemplar embodiment field kit for detecting CWAs by visual and self-reporting inspection and unmanned operation. The color of the sensor array changes when the test paper contacts the target CWA agent(s). In the shown use, military personnel 206 use individual test strips 205 by wiping the strip against a suspect surface 207. The individual MIKE-tape strip can then be inserted into a reader 203 for opto-electronic verification of any sensed CWAs by colorimetric changes of the MIKE-tape. The opto-electronic unit 203 may also be used as an unmanned detection unit. As detailed below, MIKE-tape is both more stable and has improved agent specificity over existing technology. These characteristics are obtained by cross-linking density of each polymer matrix, chelating agents, and indicator functionalization. The formulations are subjected to calibration studies and aging effect evaluation of humidity and temperature effects, as well as validation testing.

Sensor Coatings

Stability and a high degree of agent specificity are accomplished for MIKE-tape by correctly pairing chemistry of the sensor indicator with the substrate chemistry and structural characteristics. As detailed below, the optimal substrates are unexpected and non-trivial to determine. Additives may be used both for the sensor indicator and the substrate to improve the detection rapidity, stability and specificity for individual toxic agents. Exemplar additives described herein include hydrolyzing agents for improved performance of indicators in low humidity condition, such as bisphenol-a (BPA) and free-volume enhances or FVEs to improve the stability and cladding of the indicator in substrate polymers.

Indicator Chemistry

In exemplar embodiments, MIKE-tape suitable indicator chemistries are based on acid-based Lewis indicators or redox indicators. Examples of suitable Lewis indicators include cresol red, bromothymol blue, bromocresol purple, Congo red, or ethyl violet, selected based on specific applications. Examples of suitable redox indicators include dipyridines, benzidines, diphenylene diamine, or metalloporphyrins, also selected based on specific applications. The first indicator system results in color change upon reaching equilibrium with the target gases.

Improved specificity performance of the selected indicators is achieved in various embodiments by specific additives that target the equilibrium at the pKb and pKa according to the indicator and target gas reactions. Redox indicators are based on a non-reversible reaction with the target gaseous species resulting in irreversible color change.

The immobilization of this indicator/activator chemistry into a polymer matrix often offers tunable aprotic media for the interaction of the indicator and the target gas. The choice of the three components (indicator, activator, and polymer), in addition to their ratio, is chosen in various embodiments of MIKE-tape according to the reactivity and specificity of the sensor cladding.

Figure 3:
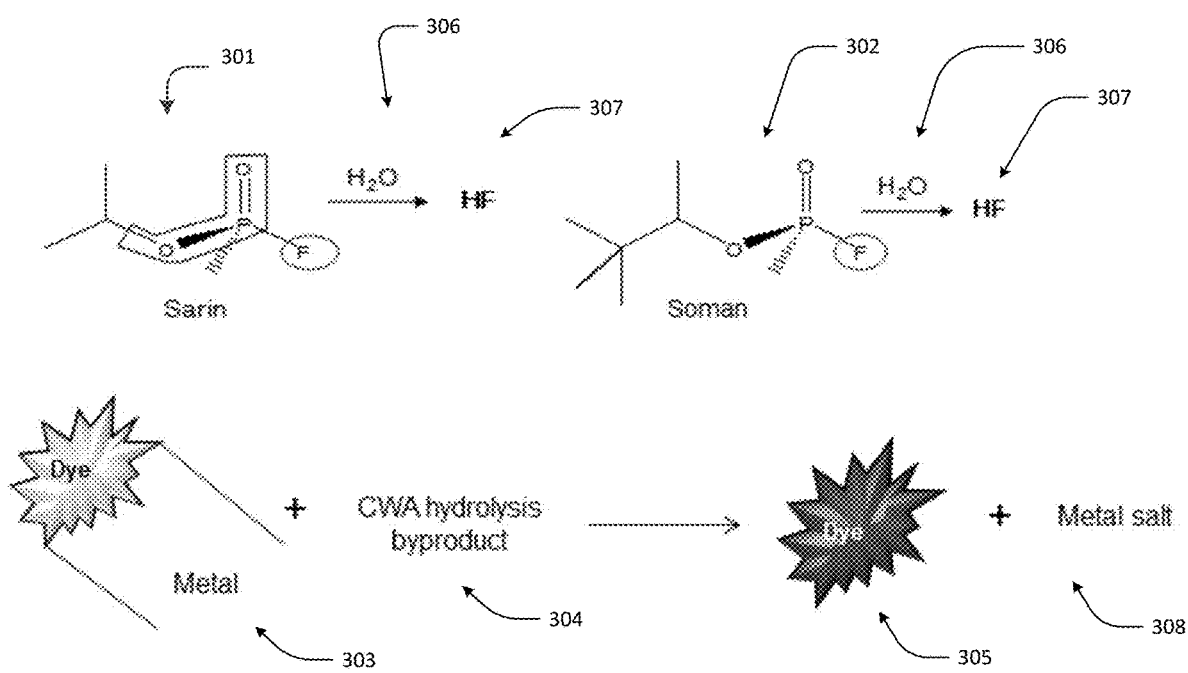
FIG. 3 shows the chemical mechanisms for the detection of CAVA toxins sarin and soman.

Development of optical-based sensor claddings against CWA vapors produced an unexpected and unique indicator composition that works by competitive binding of CWA hydrolysis byproducts. FIG. 3 shows the mechanism of chemical agent hydrolysis (with sarin and soman as examples) and the subsequent detection by disclosed colorimetric competitive indicators. As shown in FIG. 3, sarin gas 301 hydrolyzes or decomposes when exposed to water vapor 306 to release HF. Soman gas 302 similarly hydrolyzes or decomposes when exposed to water vapor 306 to release HF 307. In various embodiments, an applicable indicator dye is complexed with a metal salt 303 that remains stable within the cladding but reacts in the presence of the CWA hydrolysis byproduct (such as HF) 304 to release the dye 305 from the metal salt 308 thereby exhibiting the colorimetric properties of the dye. In certain embodiments, a hydrolyzing agent is utilized as an additive to improve the effectiveness and reaction or detection speed in low humidity environments. An exemplar tested hydrolyzing agent is bisphenol-a. Disclosed in application Ser. No. 14/089,627 and incorporated herein is a colorimetric technique for CWA vapor sensing, and specifically for GB and GD early warning. Calibration plot for CWA sensor substrates were generated as the sensor formulations were tested against their target analytes in the gas phase, balanced with clean air to create the desired concentrations. Specifically shown in FIG. 3 are examples of chemical warfare agent structures (sarin, soman) and molecules released in their hydrolysis.

Figure 4A:
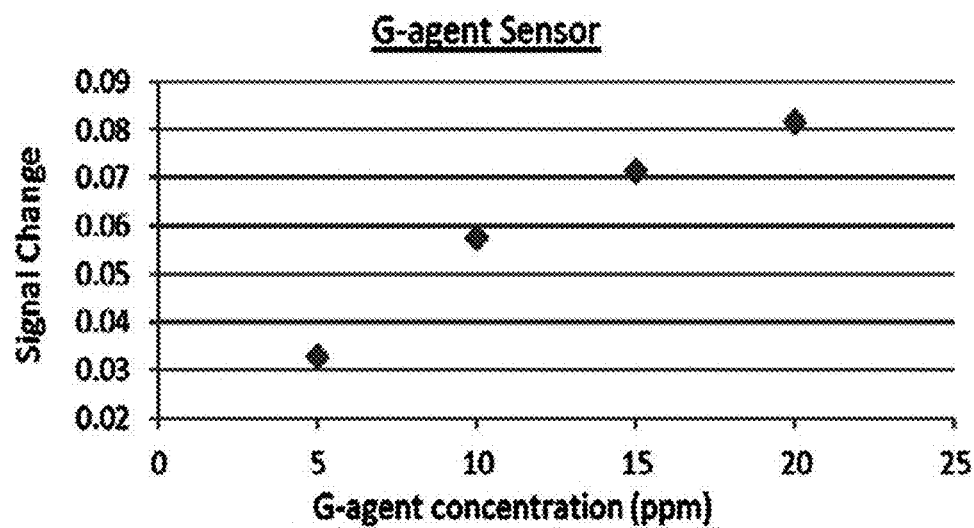
FIG. 4A-C show the results of selected agent detection at given concentrations.
Figure 4B:
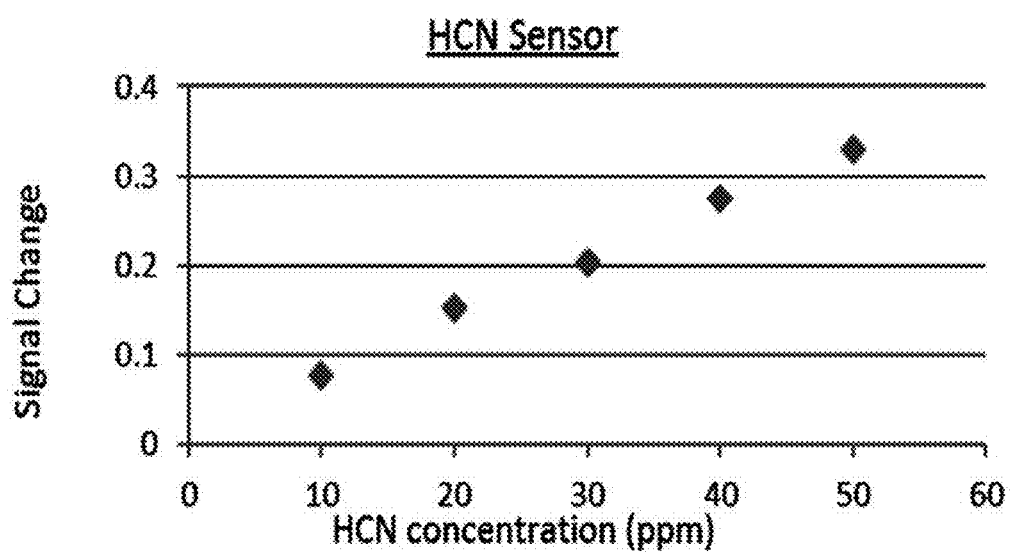
Figure 4C:
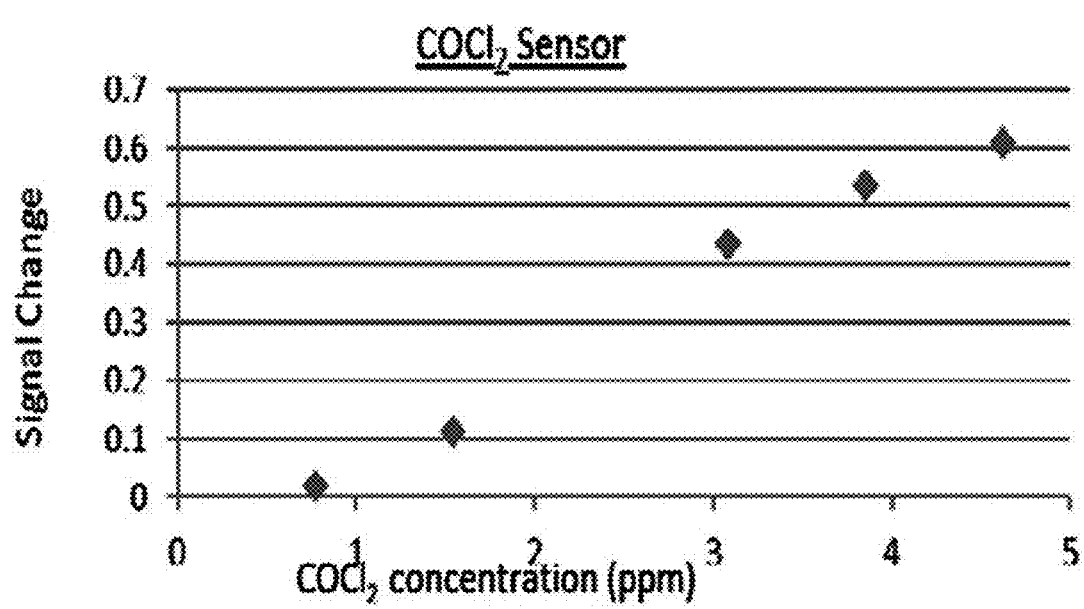
Figure 5:
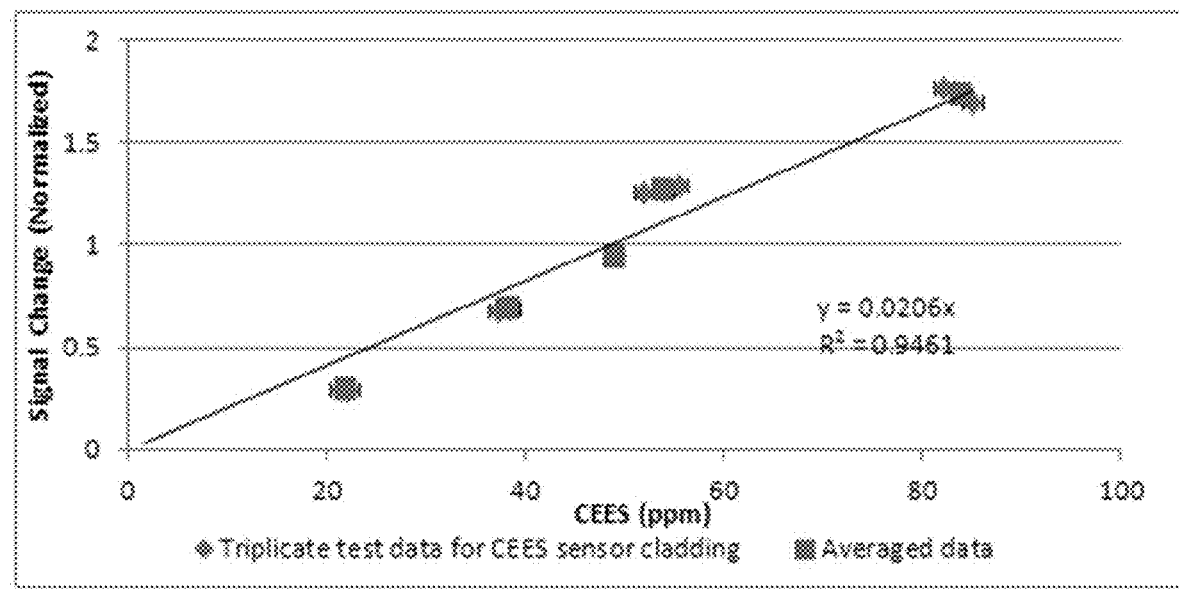
FIG. 5 shows the results of chloroethyl ethyl sulfide ("CEES") detection at given concentrations.

FIG. 4A shows the GB/GD sensor calibration with DFP simulant at 20, 15, 10, and 5 ppm. FIG. 4B shows results of a GA sensor coating calibration using HCN in the gas phase. FIG. 4C shows results of phosgene sensor calibration. Shown in FIG. 5 are the results of half mustard (CEES) sensor calibration.

Effects of Temperature and Relative Humidity on Sensor Array Performance

Figures 6A, 6B:
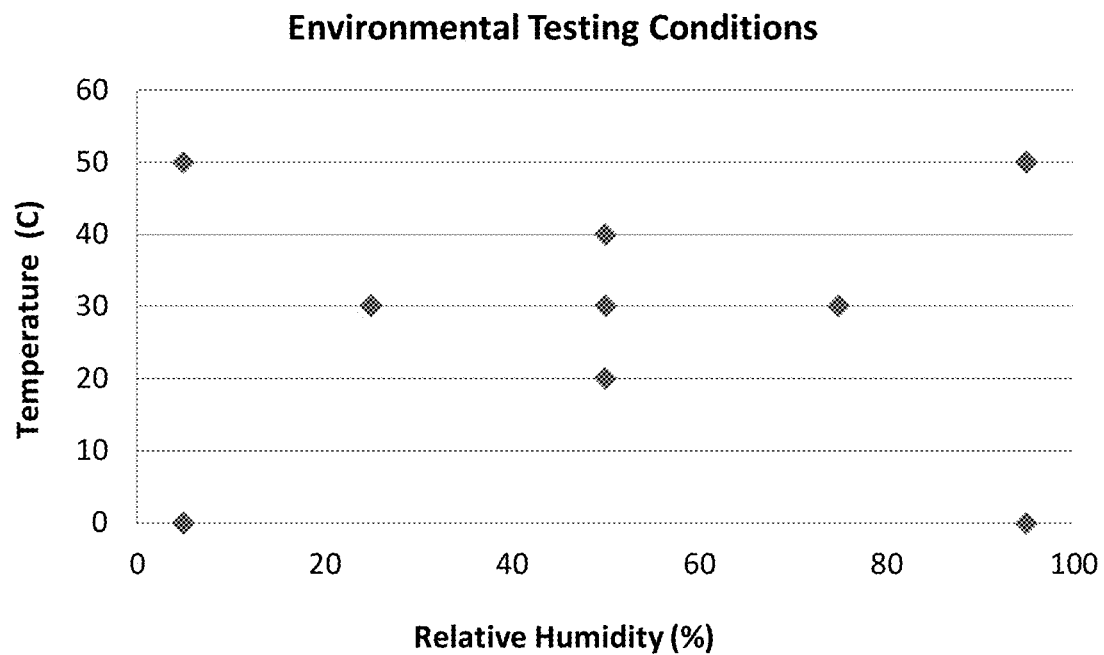
FIG. 6A-B show a plot and table of humidity and temperature validation testing points.

An exemplar fully integrated sensor array was tested against the range of temperatures and relative humidity levels as charted in FIG. 6A following the design of experiment (DOE) matrix shown in the table of FIG. 6B. For certain embodiments, this testing served to quantify the effects of temperature and humidity on sensor array sensitivity as a basis for baseline correction algorithms. Four sensors (HD, GB/GD, GA, and CG) are exposed to all nine test conditions to validate the chosen indicator and substrate combination for an embodiment.

Figure 7A:
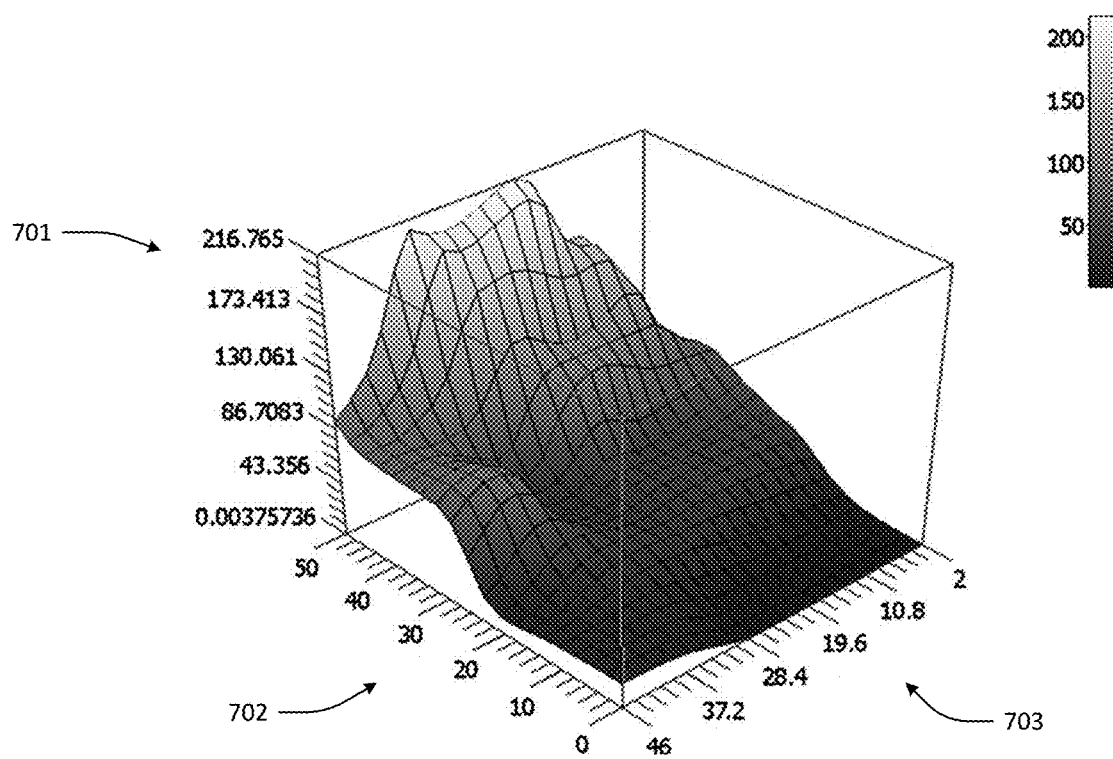
FIG. 7A shows sensor results after exposure to CEES at given temperature and humidity conditions. Sensor output is shown depicted on the z-axis.
Figure 7B:
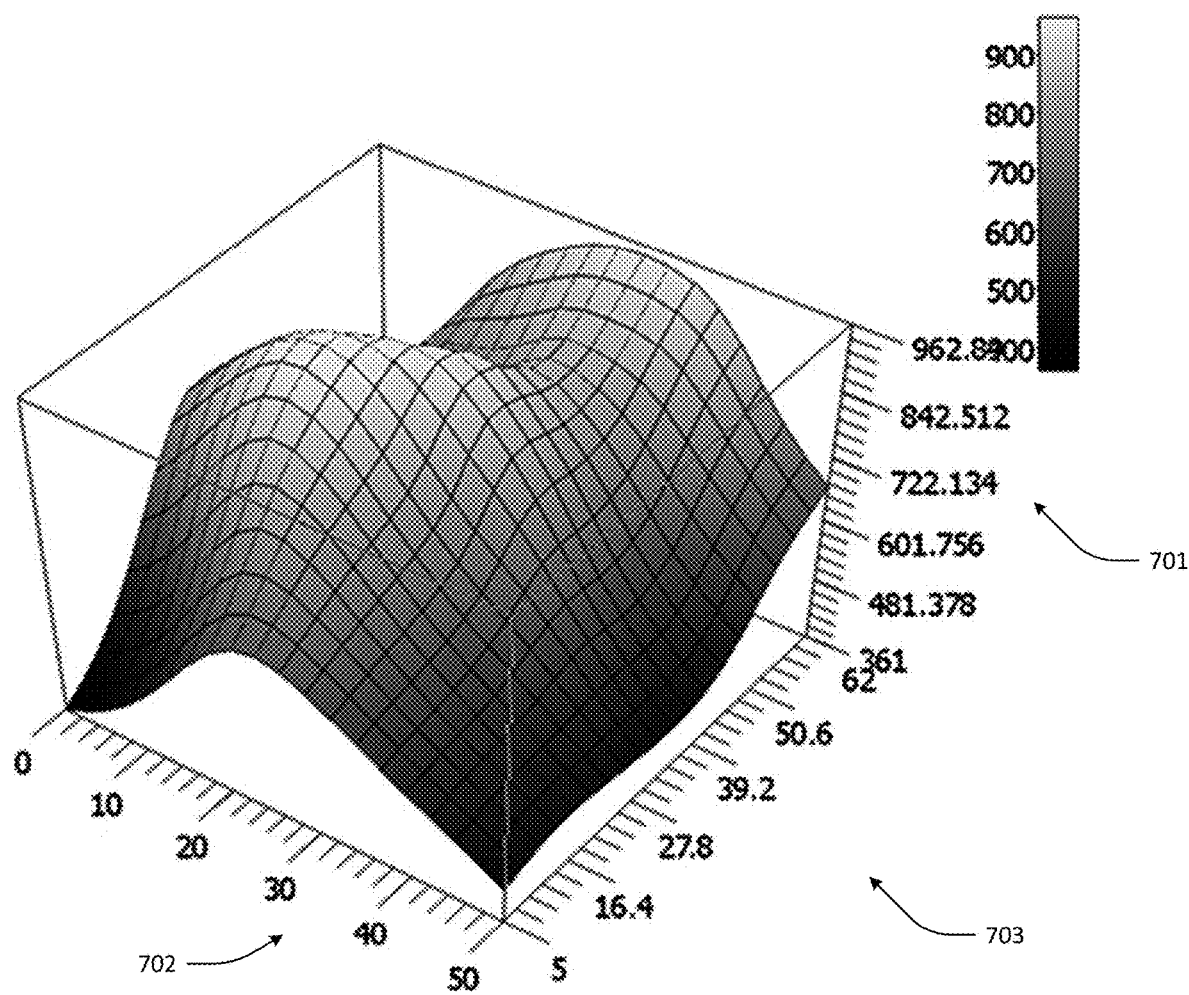
FIG. 7B shows sensor results after exposure to 5 ppm Phosgene (CG) at given temperature and humidity conditions. Sensor output is shown depicted on the z-axis.
Figure 7C:
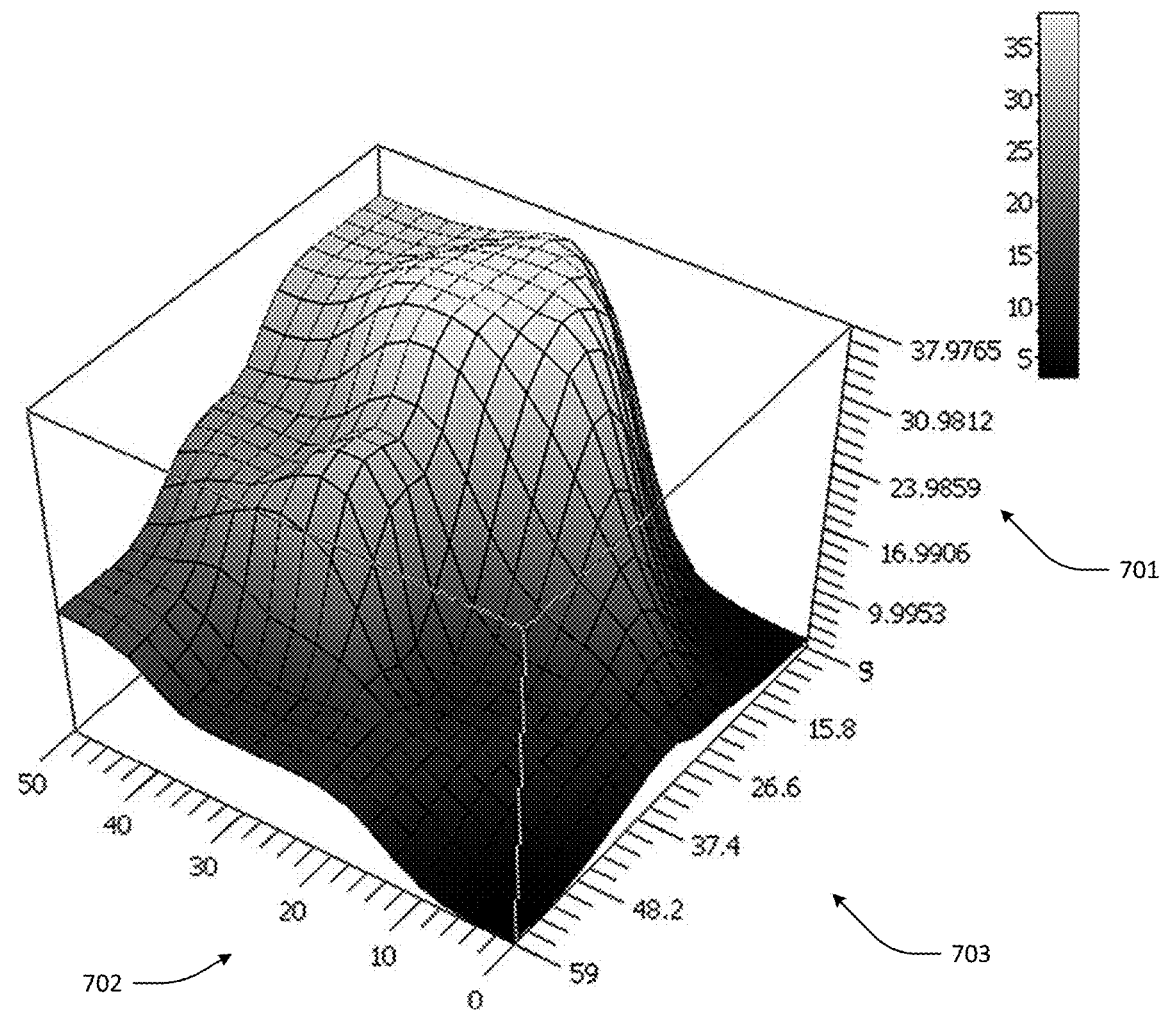
FIG. 7C shows sensor results after exposure to DFP at given temperature and humidity conditions. Sensor output is shown depicted on the z-axis.

FIGS. 7A to 7C illustrate an exemplar CWA vapor sensor array response (absorption changes) generated with QtiPlot Random XYZ Gridding function, using the Shepard (uniform data) model. The measurements are given in mV or intensity counts. Generally, there is a higher response at higher temperatures, and lower response at lower temperatures. Sensor output 701 is shown against temperature 702 and relative humidity 703. These trends were used in designing and modeling the signal processing algorithms. The results were consistent with CG and HCN sensor performance, where lower temperatures slow gas diffusion into the sensor cladding. Temperature compensation factors have been extracted from this data and further integrated into the concentration measurement model.

Optoelectronic System

Figures 8A, 8B:
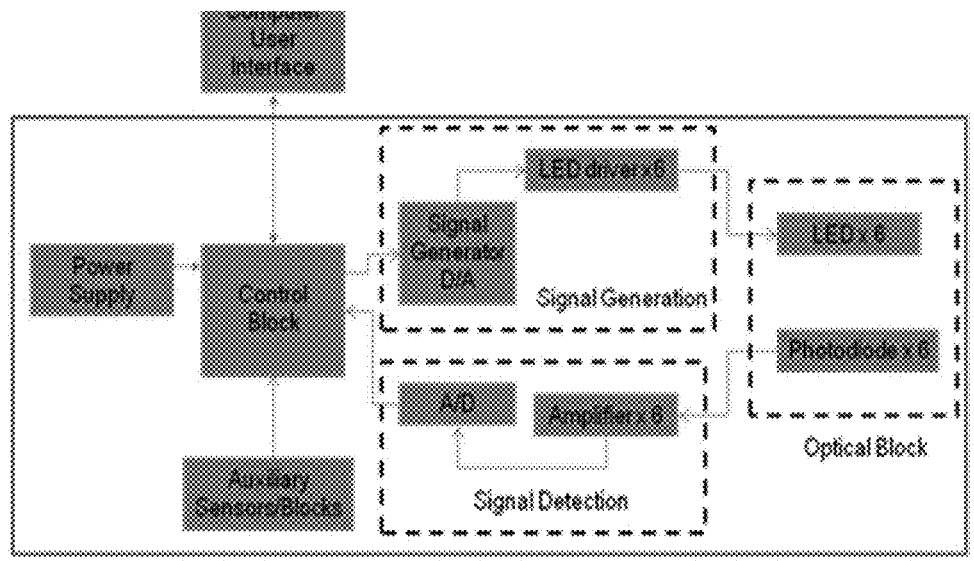
FIG. 8A is a component diagram for an opto-electronic reader.
FIG. 8B is a chart of target agent concentration boundaries.
Figure 9A:
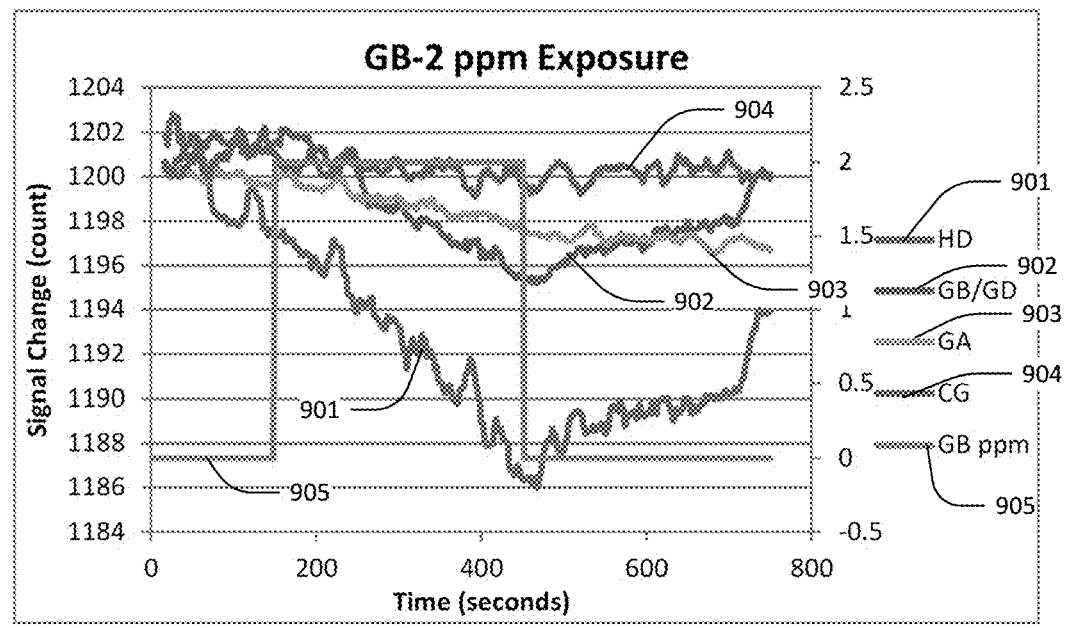
FIG. 9A-9C depict sensor array results from exposure to 2 ppm (FIG. 9A), 10 ppm (FIG. 9B), and 20 ppm (FIG. 9C) sarin (GB) vapor in a 50% relative humidity air stream. Output results for each of the sensors are shown for cross-reactivity.
Figure 9B:
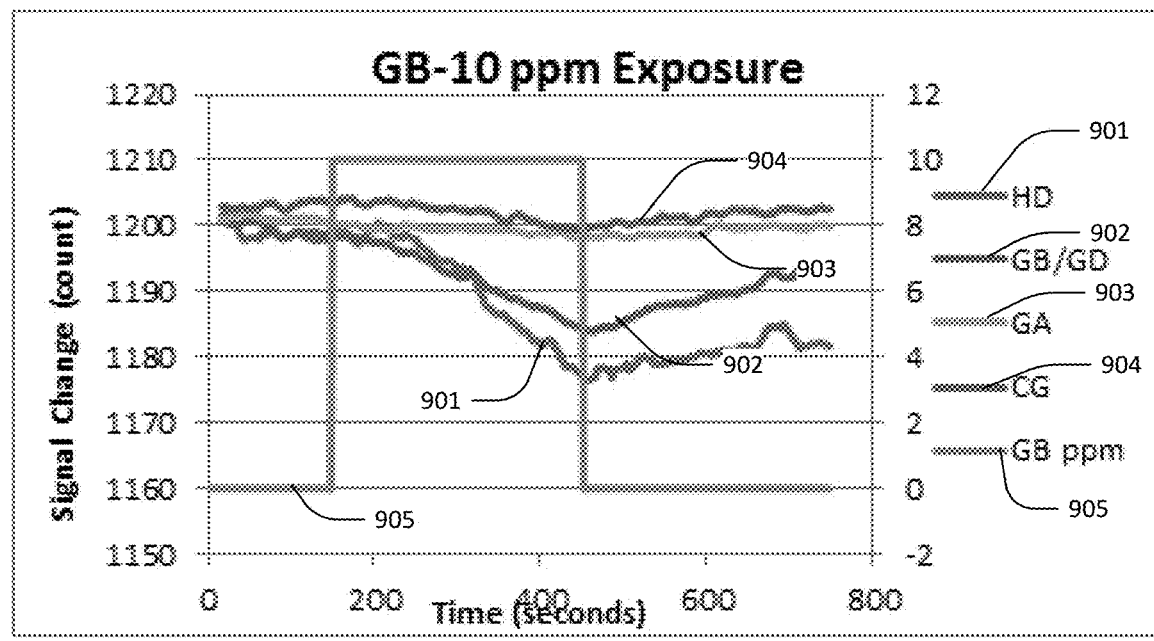
Figure 9C:
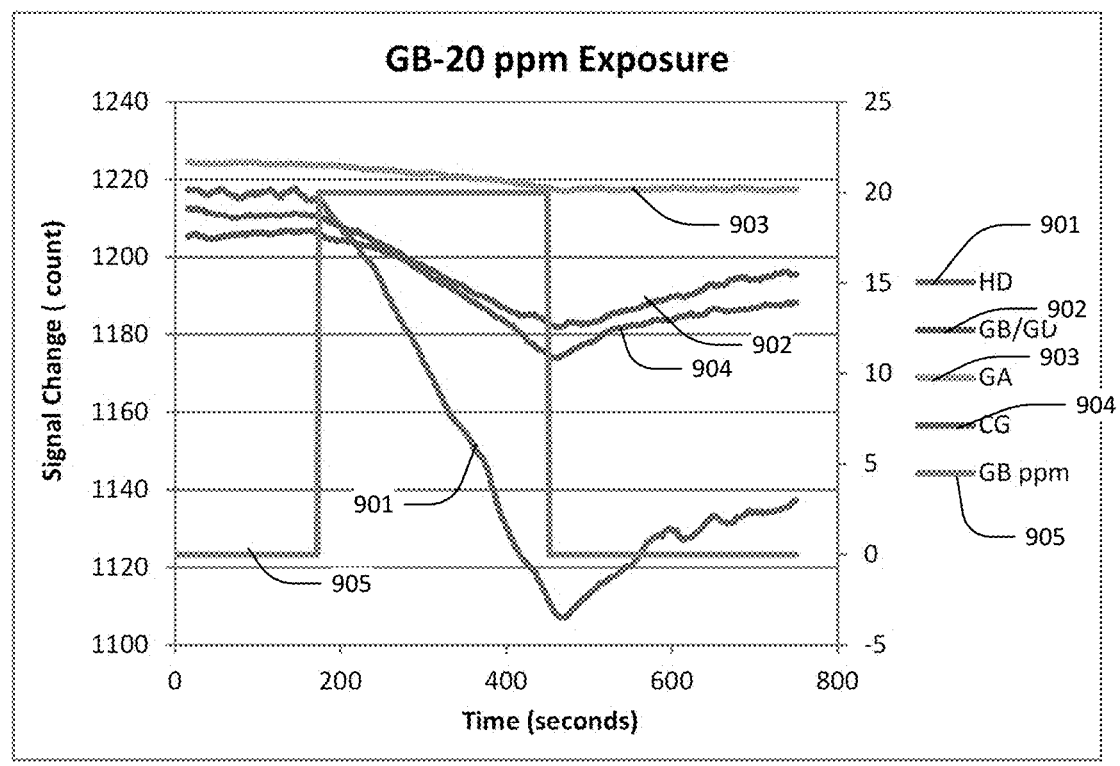
Figures 10, 11:
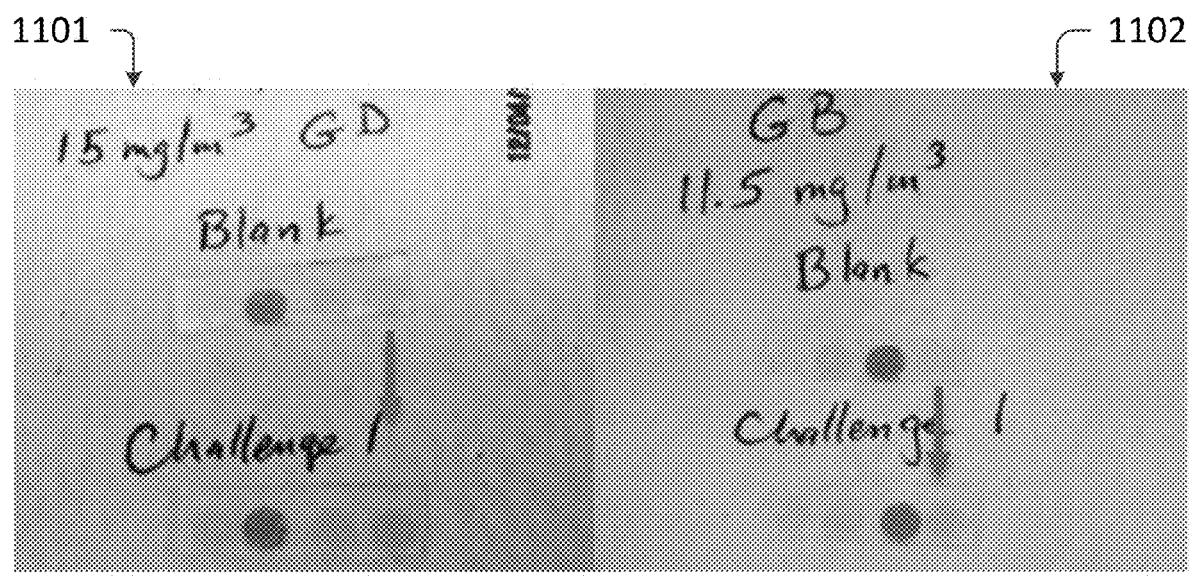
FIG. 10 is a chart of G-agent concentration equivalencies.
FIG. 11 shows results of sensor array exposure to 10 and 20 ppm of GB/sarin and GD/soman.

As described above and shown in FIG. 2, in certain embodiments MIKE-tape is implemented as a field detection kit for personnel or for unmanned operation. These implementations may utilize an optoelectronic system to read the colorimetric changes in the MIKE-tape sensors. The component diagram in FIG. 8A depicts an exemplar reader which is designed for a compact ruggedized housing (<0.5 ft.$^3$), and operation at temperatures ranging from 0° C. to 55° C. and at 10%-90% humidity. As designed this unit is ready for operation less than 30 seconds after power-up. The power-up time is required for self-calibration, and for the power output from the LEDs, and to stabilize the temperature of other electronic components. The system diagrammed in FIG. 8A is designed for four-channel optoelectronic operation for self-reporting in the event of HD, GB/GD, or GA chemical release in the ranges shown in FIG. 8B.

The optoelectronic reader unmanned embodiment is designed for unattended operation, eliminating the need for inspection of test papers such as M8 paper. The system components were selected based on anticipated environmental conditions such as temperature fluctuations from −40° C. to +80° C., and relative humidity from 5% to 95% RH. The setup was tested and validated with the selected sensor coatings.

A process was developed for validation testing of the system self-reporting system for chemical warfare agent aerosol/vapor detection. The sensor array was integrated into a commercial detector evaluation system and tested for proper functionality. In the validation process, the sensor can alternately sample clean air and challenge vapors. Challenge vapors were generated by passing a nitrogen stream over a small amount of liquid chemical agent (in an impinger bubbler) and diluting as needed with clean dilution air to reach the desired concentration. Challenge vapor concentrations were measured and verified using a commercial (MINICAMS) automated gas chromatography system.

The sensor substrates were prepared and packaged on a replaceable cartridge for mounting onto the optoelectronic device for gas sampling and optical signal collection. In order to evaluate and determine the level of detection of our unattended sensor array for vapor detection, the chemical sensor array was tested against several live agents—GB, GD, HD, VX—at varying concentrations in a commercial setup.

Results of GB exposure from the testing are shown in FIG. 9A-9C, where GB sensor coatings were tested at concentrations of 2, 10, and 20 ppm (11, 55, and 110 mg/m$^3$) at 50% relative humidity at a validation test lab (ECBC and CUBRC). The testing process consisted of exposure to 2.5 min. of clean air, 5 min. of agent gas, and 5 min. of clean air for recovery and cleanup. The CWA concentrations were higher than is typical in vapor detection testing setups, since the system is meant for unattended outdoor monitoring similar to conditions described for M8 test papers. Some cross-reactivity was noticed with the HD sensor coating, which could be attributed to sensitivity modifications to the sensor chemistry to improve sensor sensitivity.

The table FIG. 10 presents the test matrix and the approximate range of vapor concentrations targeted for each chemical agent. The tests were performed at ambient environmental conditions (measured and recorded). The target matrix acts as a starting point, and test results may be utilized to iteratively optimize concentrations by deviating from the planned concentrations.

In live agent testing, the colorimetric sensor arrays were exposed to sarin (GB) and soman (GD) nerve agent vapors according to concentrations shown in FIG. 10. Repeatable results were obtained with GD and GB as shown in FIG. 11.

Evaluation of Sensor Array Analytical Characterization

Performance of the optoelectronic MIKE-tape reader is measured according to system performance characteristics and targets shown in FIG. 12.

A number of chemical sensing technologies have been investigated for remote chemical sensing including UAS copters. For many of these technologies, the power, weight, and size requirements make them unsuitable. As a solution to many of these and other problems with current methods discussed in this application, disclosed is a simple sensor cladding passively integrated onto a camera lens for colorimetric monitoring. In certain embodiments, the camera is mounted on a UAS “copter”. The utilized sensor cladding technology is based upon selecting colorimetric indicators for maximal contrast, custom cross-linking polymers for optimal diffusion of each target chemical, and activators that selectively bind to the target analytes, making these detector coatings superior to other colorimetric sensors.

Additionally, most such current detectors are not good for sensing chemical agents while the sensor is in motion, specifically at typical UAS copter maneuvering speed. Tests have demonstrated highly reliable optical coatings sensitive to a number of chemical agents and toxic chemicals, which will be extended to remote sensing on mobile connected camera, such as may be mounted on UAS quadcopters.

Integration with currently available UAS systems is straightforward, with passive sensor tape that does not require a hardware interface, flexibly adaptable to many robots including UAS's. A prototype system demonstrated ammonia sensors as an exemplar implementation of MIKE-tape utilized on a UAS. These results are detailed below.

Figures 13, 14A:
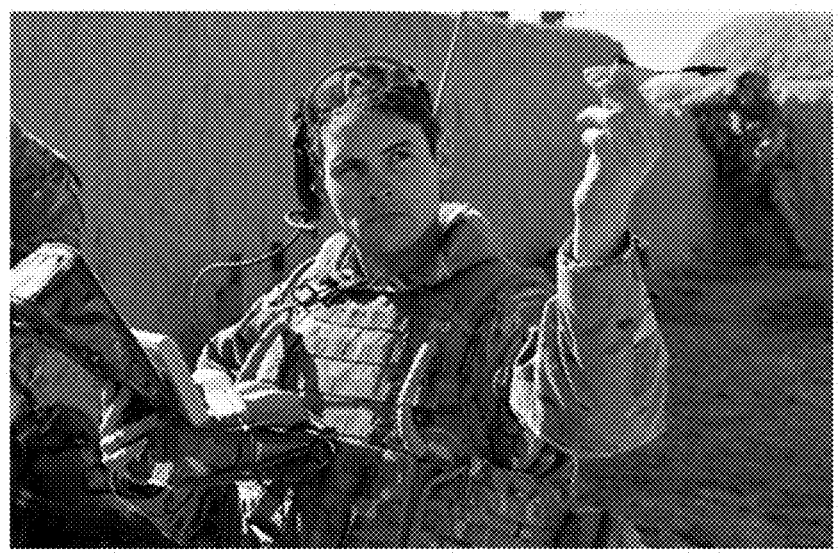

In an exemplar embodiment, a piece of clear tape spotted with chemical indicators is applied over the down-looking camera sensor; distance viewing is retained. The camera and the system operator will see the change without additional readout or communication electronics, as illustrated in FIG. 13. FIG. 13 shows Sergeant Scott Weaver launching a Black Hornet Nano Unmanned Air System from a compound in Afghanistan.

Polymer Matrix Substrates

For typical embodiments, sensor claddings consist of optical grade polymers immobilized with colorimetric and/or fluorescent indicators that undergo optical changes upon exposure to their target analyte.

The cross-linked polymers are based on a chosen urethane acrylate polymer, co-polymerized with a silicone backbone such as dimethyl siloxane, which in general is chemically inert, yet leaves the polymer with the large free-volume necessary for rapid target diffusion. Exemplar polymers are shown in FIG. 14A and FIG. 14B. The highlighted polymers from FIG. 14B were identified as having optimal performance in tested MIKE-tape embodiments.

The polymer is cured after immobilization with target indicator mixture, and simultaneously cross-linked by UV light or heat. The monomer's functionality gives the polymer enough polarity so that it is compatible with indicator immobilization and does not interfere with color rendering. If the cross-linking is too high, the polymers become tough, hard, and impervious. If the cross-linking is too low, the polymers are soft and weak, and too highly permeable. Therefore, the cross-link density must be balanced between toughness and permeability.

Optimum colorimetric indicator systems are indicated by immobilizing the target indicators into UV-curable polymeric claddings. The polymer cladding is selected based on its cross-linking density (referred to as the monomer:oligomer ratio), mechanical properties, adhesion coefficient, and indicator compatibility. The table in FIG. 14A lists Raymet polymers evaluated for suitability. The table in FIG. 14B a full list of tested polymers. The highlighted polymers 690-4 (polymer J) and 144-28-3 (polymer F) were identified as optimal.

Free Volume Enhancer Additives

The immobilization indicator/activator(s) into selected polymer matrix though the use of proper solvent mixture, is further optimized with the addition of free volume enhancers to improve the porosity of the cured polymer matrix allowing higher diffusion characteristics to the target gas.

An effective way to tune the gas diffusion and moisture content is to add free volume enhancers (FVE) to the polymer matrix.

FVEs are modified poly (styrenesulfonate) (PSS)-derivative chemical compounds (FIG. 15A) that are highly compatible with many silicone and acrylate polymer matrices. In vaiour embodiments, derivatives of these FVEs mis used to increase the free volume (polymer porosity) in order to enhance gas diffusion, and hence response speed. Such as but not limited to, PSS-octa [(3-hydroxypropyl)dimethyl siloxy] substituted, PSS-(2-(trans-3,4-cyclohexanediol) ethyl)-heptaisobutyl substituted, and PSS-trisilanol-isooctyl substituted, were evaluated as suitable sensor claddings.

Figure 15A:
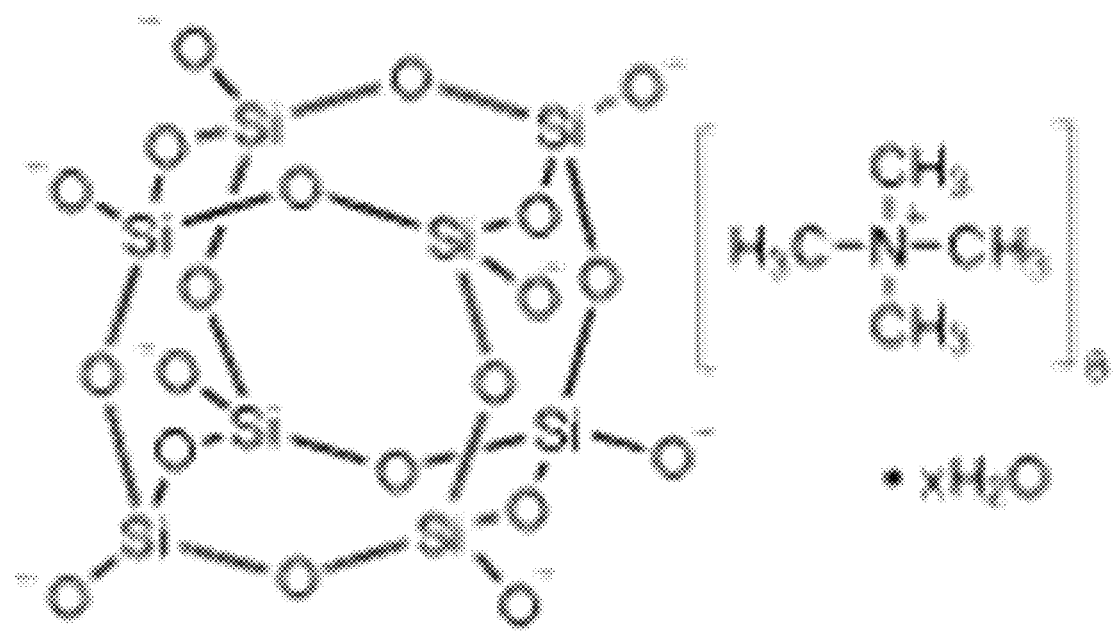
FIG. 15A shows the chemical structure of a PSS-based free volume enhancer FVE derivative.
Figure 15B:
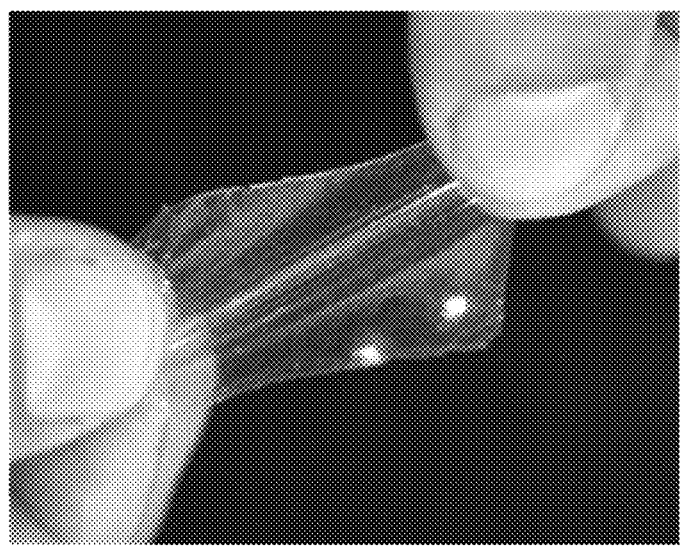
FIG. 15B shows an exemplar MIKE-tape sensor cladding.

Further enhancement of the coating cross-linking will increase measurement range, sensitivity, and long-term stability, and shorten response time. These parameters are optimized for the overall system response criteria. In one embodiment, optimization is performed by adding free volume enhancers (FVE) to sensor cladding formulations. The function of this additive is to open the polymer cross-linking structure, as shown in FIG. 15A, increasing the diffusion rate, response speed, reactive surface area, and consequently the sensitivity. A photograph of this sensor cladding exemplar MIKE-tape is shown in FIG. 15B.

Figures 16, 17:
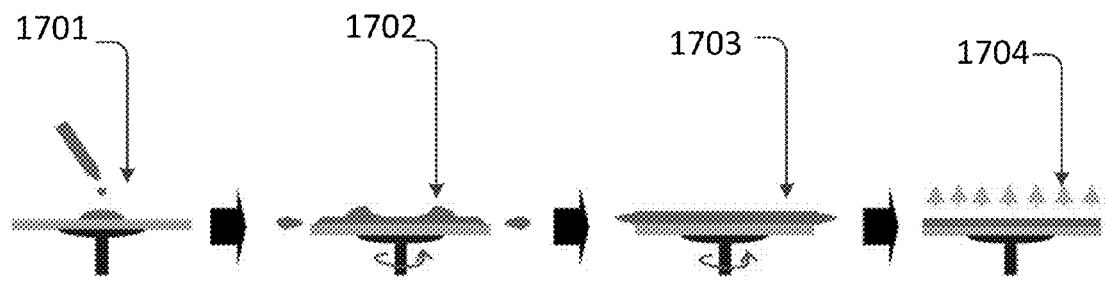
FIG. 16 shows the illustrated color scheme for coatings for chemical agent detection.
FIG. 17 shows the process steps for coating the substrate.

FIG. 16 illustrates the color scheme of target agent interaction with developed dye chemistry immobilized into custom designed polymer coatings. Various embodiments available include single or multiple combinations of six sensors for target chemicals ($NH_3$, $Cl_2$, and HCN) and chemical agents (GB/GD, HD, and Vx). As indicated above, the selectivity and reactivity of the selected dyes depends significantly on the choice of polymer matrix in terms of:
- diffusion characteristics of the target agent;
- stability of the immobilized dyes against temperature, moisture, and aging;
- cross-reactivity towards other chemicals.

Optical Coating Design and Mounting

Developed cross-linked polymers are selected and designed for each target analyte, and their diffusion properties are tuned to optimize coating sensitivity, selectivity, response speed, and stability. These polymers are based on urethane acrylate polymer, co-polymerized with a silicone backbone such as dimethyl siloxane, which in general is chemically inert yet leaves the polymer with the large free-volume necessary for rapid target diffusion.

Free volume enhancers (FVE) are selected based on the initial diffusion characteristics of the cross-linked polymers. The addition of FVE contributes to the sensor coatings in two ways: the first is to increase the open structure of the cured polymers (increasing the porosity of the polymer matrix); the second is that the functional groups in the FVEs can tune the pH of the polymer, increasing the hydrolyzing effect of the analyte, or the chelating effect of the hydrolysis by-product, and therefore pushing the reaction kinetics forward.

The polymer formulation is cured after immobilization with the target indicator, FVE, and other additives, and simultaneously cross-linked by UV light or heat. Colorimetric functionalized cladding for high selectivity is shown in cross-reactivity testing of a multiplexed sensor matrix developed for first responders.

Each indicator system is optimized for high selectivity without the need for sophisticated pattern recognition as in non-specific dot-array techniques.

FIG. 17 shows the steps of applying formulated sensor cladding onto supporting substrates (glass, quartz, or adhesive tape), spin-coating, and curing with heat or UV.

Figure 18:
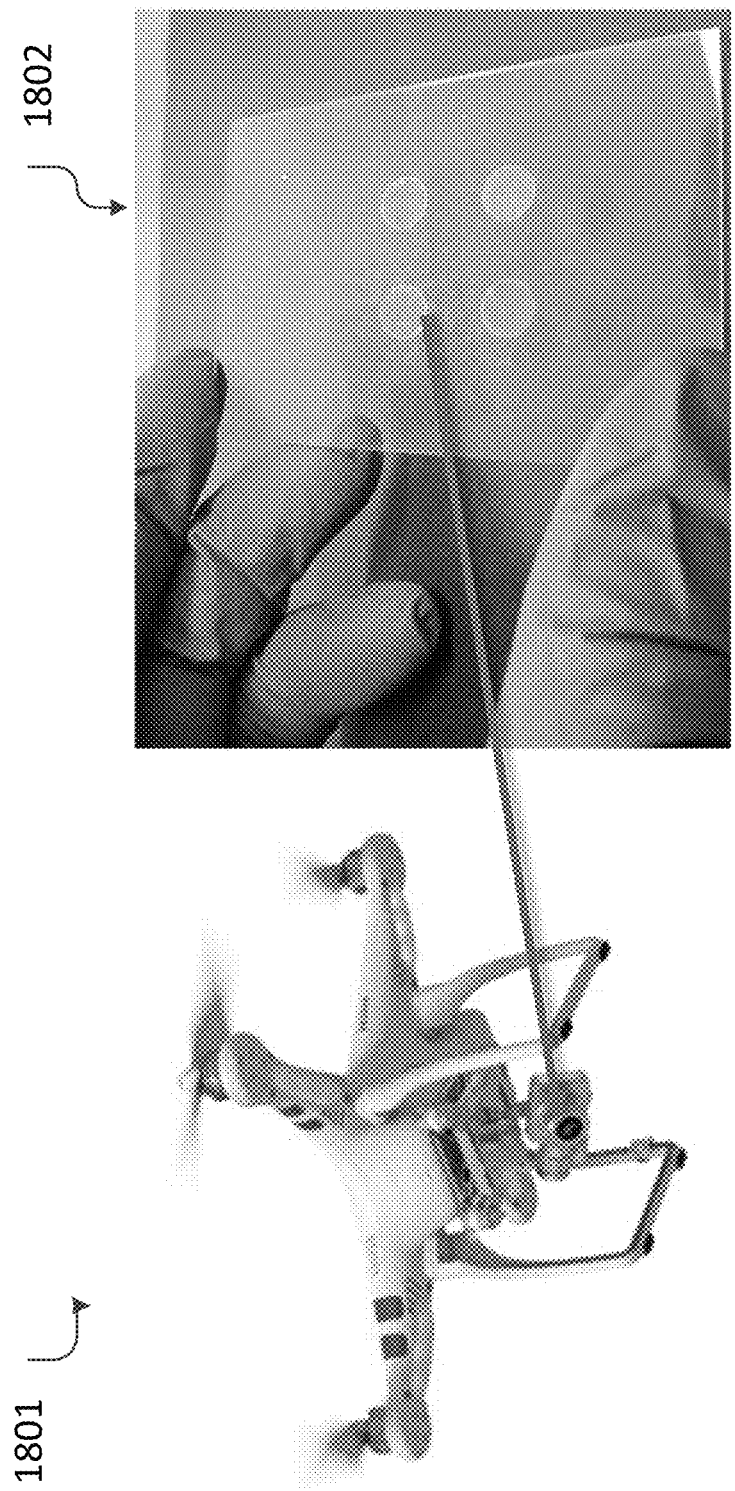
FIG. 18 shows phantom standard quadcopter for MIKE-Tape integration and testing and examples of sensor tapes for placement onto the camera.

The coating thickness is typically controlled by the solids content of the polymer formulation and the speed of spin-coating. The film thickness is typically optimized for both the desired degree of optical density change and response speed. In an embodiment using a UAS as the system platform, the optimized film is placed onto the copter camera, as illustrated in FIG. 18. FIG. 18 shows on the left a test platform 1801 and embodiment DJI Phantom standard quadcopter for MIKE-Tape integration and testing. Shown on the right are exemplar MIKE sensor tapes for placement onto the camera 1802.

Multiplexed Detection through Patterned Tape

The sensor claddings may be fabricated at large scale by a deposition technique that is capable of yield >500 sensor elements per day. This precision fluid dispensing system consists of a precision micro-syringe applicator and servo-controlled X-Y-Z translation stage (adapted from equipment designed for the biosensor market). With precise control over positioning and dispense rates (micrograms/millimeter), this technology is suitable for laying down precise amounts of viscous sensor polymer in linear arrays in the scalable fabrication of chemical reagents with 10 µm resolution; this machine could easily be adapted to produce ten or more sensor channels if needed.

Figure 19:
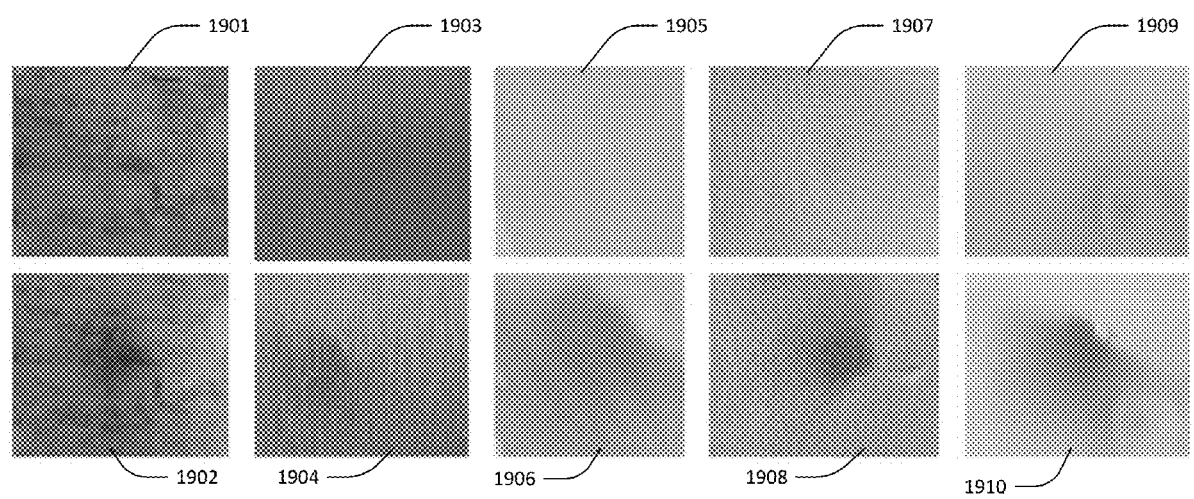
FIG. 19 shows GB sensor coating applied onto five substrates.

The disclosed sensors have been effectively fabricated onto a variety of surfaces, showing good adhesion, continuing reactivity, and sensitivity. These surfaces were coated with GB sensor cladding, and the color change was noticed upon exposure to DFP (GB simulant) in the vapor phase (FIG. 19). The adhesion to different matrices did not affect the sensing performance of the claddings.

FIG. 19 shows GB sensor coating applied onto five substrates, shown before and after exposure to DFP: coated wood before 1901 and after 1902; coated metal before 1903 and after 1904; coated paper before 1905 and after 1906; coated Styrofoam before 1907 and after 1908; coated glass before 1909 and after 1910.

Sensor and Prototype Validation Testing

Developed chemical sensing thin-film claddings have been validated by US government laboratories, including Edgewood laboratories (ECBC) and that the product meets military requirements after validation and subsequent optimization, meeting targets for sensitivity, response time, low power, and wireless communication.

Drone Copters Implementation Testing

Figure 20B:
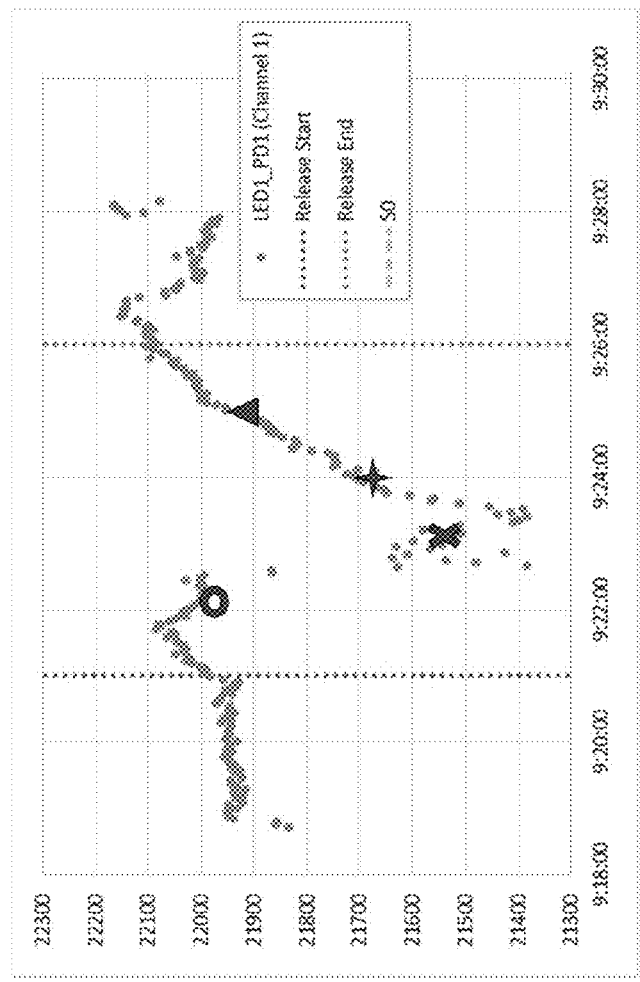
FIG. 20B shows the plot representing the time-based optical change of the disclosed sensor element during that flight.
Figure 20A:
FIG. 20A shows the path of the UAS from the starting point through a test ammonia cloud.

Highly reliable optical claddings sensitive to chemical agents and toxic chemicals have been developed. The deployment of these claddings will be extended to remote sensing placement on the MIKE-tape on remotely operated cameras such as may be mounted on UAS flying quadcopters. Integration is straightforward, with non-powered sensor tape that does not require a hardware interface. Deployment is flexible and may be adapted to a number of cameras and UAS systems. Demonstration of ammonia sensors (as a model) mounted with MIKE-tape on a UAS (InstantEye, by PSI) yielded the performance shown in FIGS. 20A and 20B. The image in FIG. 20A shows the path of the UAS from the starting point through the ammonia cloud; FIG. 20B shows the plot representing the time-based optical change of the disclosed sensor element during that flight. The plot shows how the ammonia sensor optical signal changes as the sensor maneuvers through a cloud of ammonia.

Previous work has established the feasibility of colorimetrically indicating G-type nerve agents (GB and GD) by means of colorimetric sensor cladding chemistry coated on silica glass optical fiber. The indicator chemistry in this case is sensitive to HF as a by-product of GB and GD agent hydrolysis. As described above these formulations may be adapted for MIKE-tape utilizing the described enhancements and selected polymer substrate.

Figure 21A:
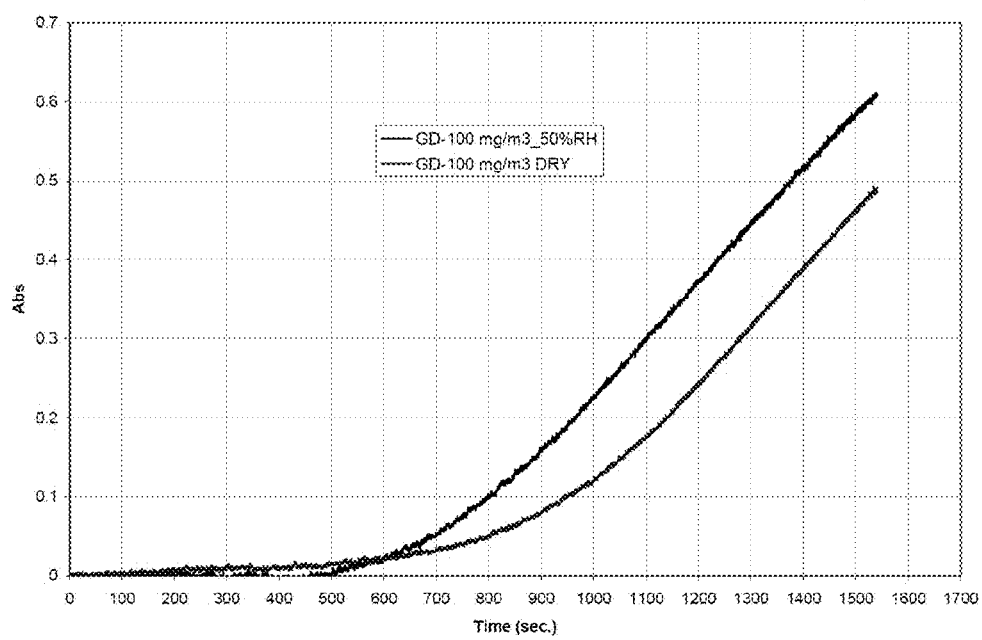
FIGS. 21A and 21B shows the results of time-based acquisition of GD and GB sensor fiber responses to 100 mg/m$^3$ in dry and humidified air by means of one-meter-long fiber, shown to illustrate the effects of relative humidity on sensor performance.
Figure 21B:
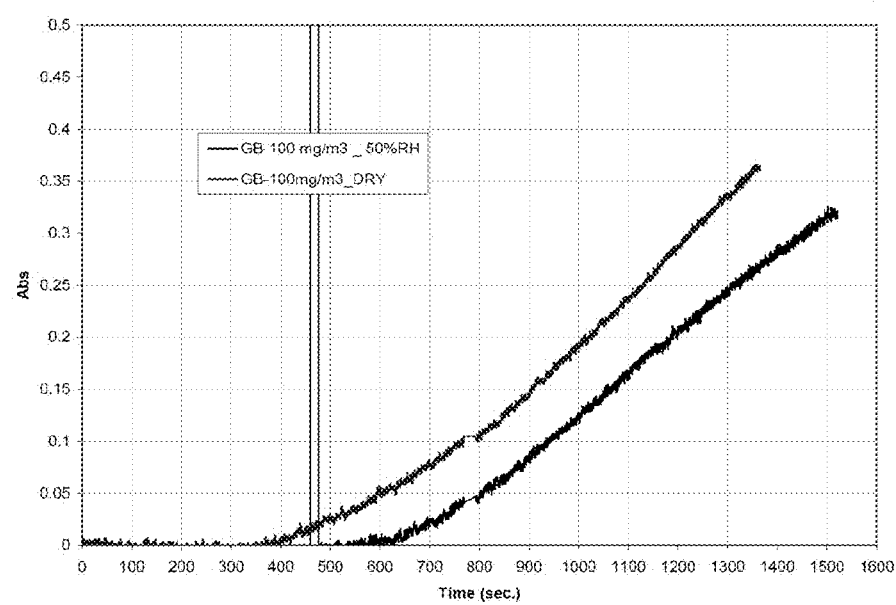

FIG. 21A-B illustrates the optical fiber cladding response over 1 m to GB and GD live agent testing at 100 mg/m³ in both dry and 50% RH air flow. These exposures were carried out with genuine samples of agent.

Previous work has also validated the performance of toxic industrial chemical (TIC) sensor arrays for first responders and environmental monitoring. Calibration plots of the performance of the current optimized sensor claddings coated on glass for phosgene, hydrogen cyanide, ammonia, and chlorine are shown in FIG. 21. These claddings are optimized for functional sensor coatings. FIG. 21 shows the results of thin film sensor coating response curves for ammonia 2101, chlorine 2102, hydrogen cyanide 2103, and phosgene vapor detection 2104.

Figure 22:
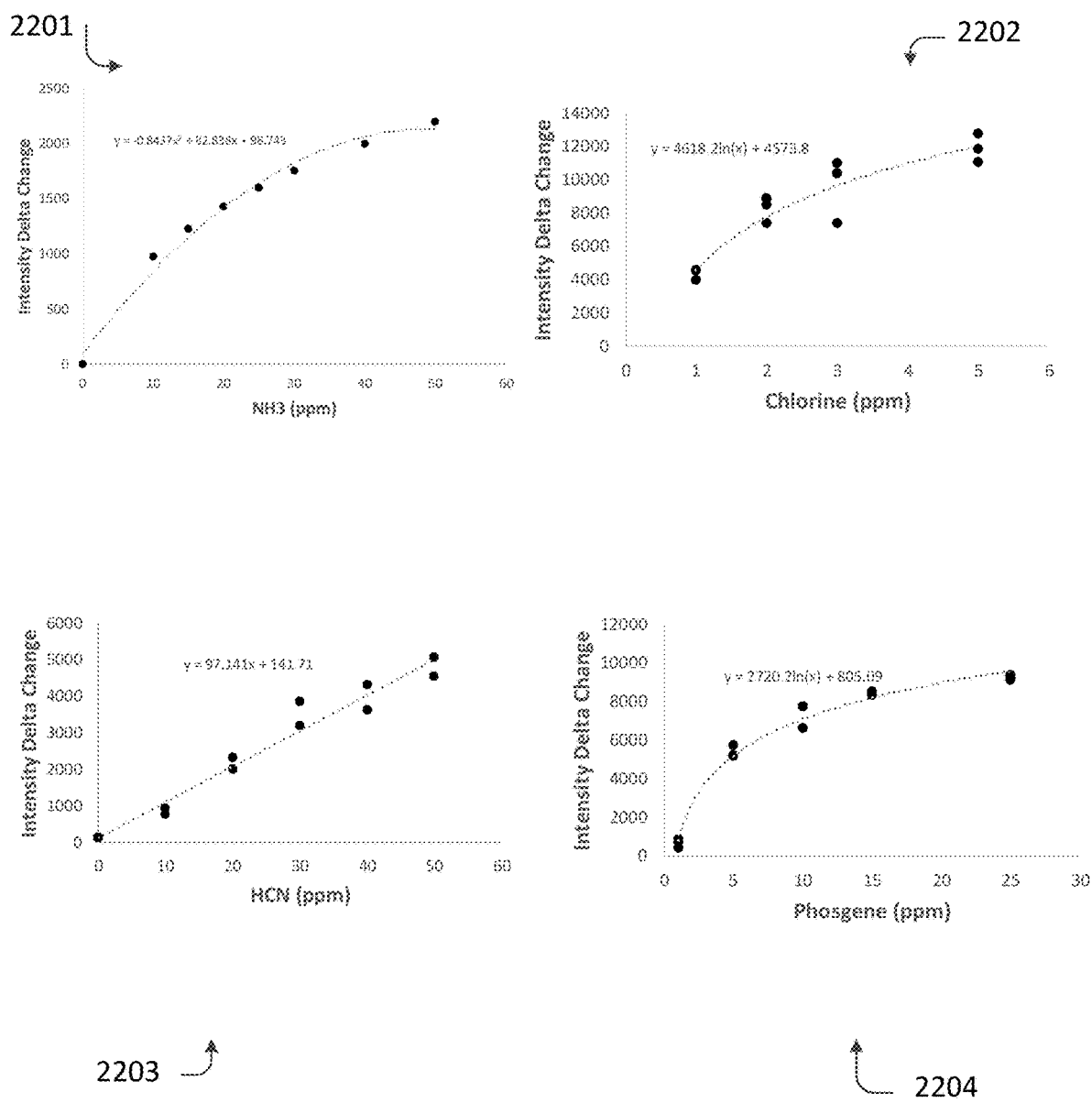
FIG. 22 shows the calibration plots of the performance of the current optimized sensor claddings coated on glass for detecting phosgene, hydrogen cyanide, ammonia and chlorine.

FIG. 22A-B show the sensor cladding response to a 10 ppm chlorine release after immersion in tap water and salt water. The photos show that our polymer colorimetric indicator for chlorine is unaffected by immersion for up to an hour in either tap water or salt water.

The chemicals and materials needed to produce the target-sensitive colorimetric sensors are disclosed. Pure polymer resins, solvents, free volume enhancers, and substrate material will also be acquired for indicator immobilization and selection of a target matrix. Agent simulants such as CEES (2-chloroethyl ethylsulfide), commonly referred to as "half mustard," and diisopropyl fluorophosphate (DFP), which are CWA simulants for sulfur mustard and soman/sarin respectively, are used for testing and validation. Initial individual sensor coatings are fabricated with white or transparent backing material, to observe the indicator response and select the most effective polymer matrix for each sensor coating.

Figure 23A:
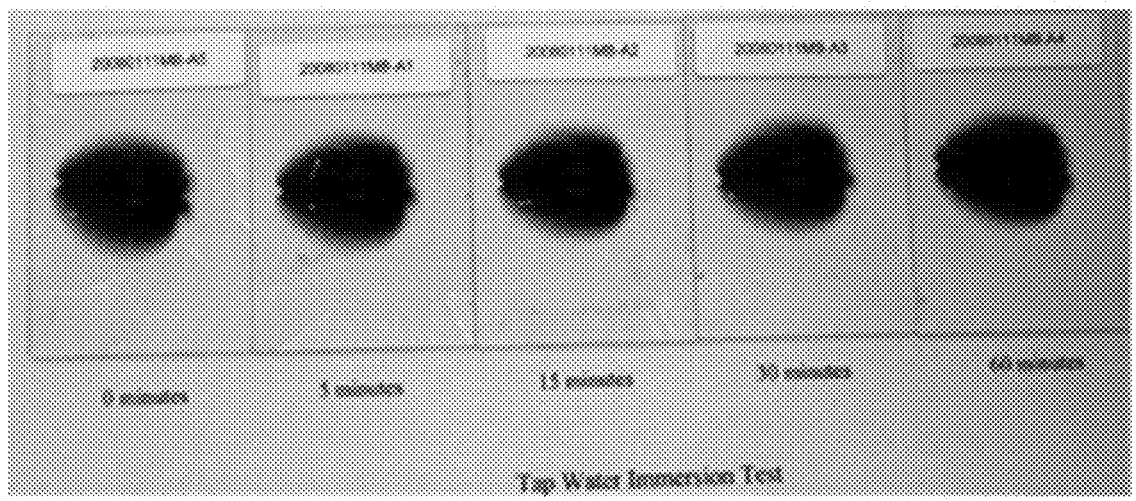
FIG. 23A-B shows the results of exposed film substrates after tap water (FIG. 23A) and salt water (FIG. 23B) immersion for 0, 5, 15, 30, and 60 minutes.
Figure 23B:
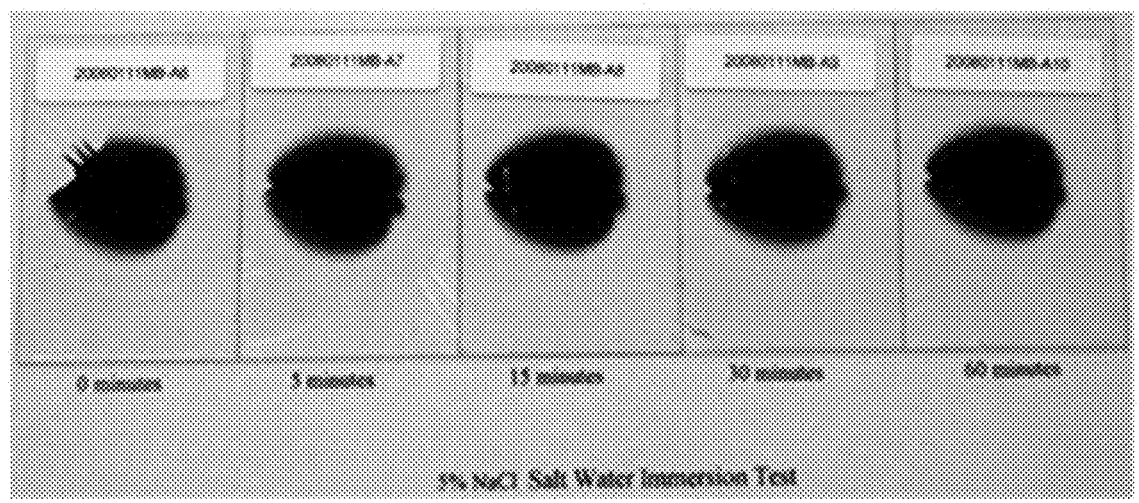

In an exemplar embodiment, single analyte sensor tapes are positioned onto the DJI Phantom copter camera lens. Each sensor tape has its colorimetric change recorded using an ocean-optic spectrometer in a controlled test, as shown in FIG. 23. In certain embodiments, additional coating optimization steps (layer-by-layer versus single-layer) are performed to establish the ultimate response on the DJI Phantom platform. Applications of this embodiment are applicable to other UAS platforms such as the PD-100 or PD-150 Hornet, PSI Instant Eye, or other UAS or UGS platform.

Testing Environment

The utilized gas testing system is modeled after those at government and commercial testing laboratories, and has been validated by West Coast Analytical Service, Inc. (WCAS) for generating precise concentrations of hydrogen sulfide mixtures. The difference between what was calculated based on generated gas (63 ppm) and what WCAS measured (66 ppm) was well within the range of expectation for this type of analysis. An engineering analysis has also been conducted of the complete gas delivery system; the analytical data included the mass controller error, an analysis of mixing conditions, and the humidity generation error. The results show that the concentrations generated have a $C_o+0.04\%$ error, which is in close agreement with the WCAS report ($C_o$ is the error associated with the labeled concentration of as-purchased gas). Therefore, the precise generation of vapor concentrations is dominated by the analytical grade of gas we purchase, which determines $C_o$. This testing system is used to generate mixtures of air with hydrogen cyanide, ammonia, and chlorine gases.

Figure 24:
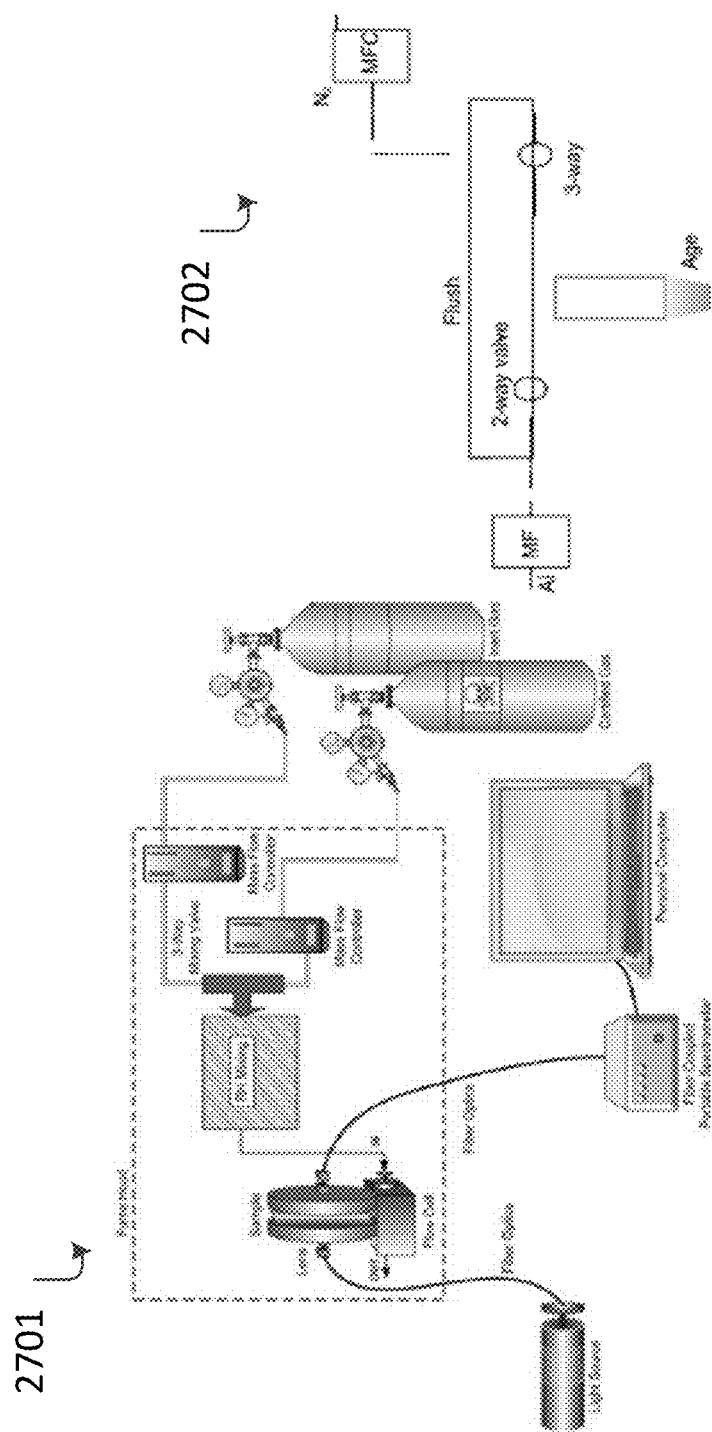
FIG. 24 shows a testing environment for a vapor generation system for use in testing MIKE-tape configurations.

Generating vapor from liquid diisopropylfluorophosphate (DFP) is expected to be subject to more fluctuations. The downstream concentration is measured with a commercial handheld photoionization detector (PID) (RAE, MiniRAE 2000) calibrated for sarin and mustard gas. A multiplicative correction factor is used according to guidelines from RAE. In the vapor generation system, a stream of pure nitrogen is bubbled through the liquid agent simulant DFP. The nitrogen then becomes a carrier gas containing the simulant vapor. The vapor concentration is modified by diluting the carrier flow with humidified air, which is then introduced to the sensor sample. The resulting color change is monitored by an optical fiber coupled to a commercially available Ocean Optics spectrophotometer, as illustrated in FIG. 24. The DFP vapor flow is measured and calibrated by means of the MiniRAE FIG. 24 shows the disclosed testing environment for a vapor generation system 2401. The vapor delivery system (VDS) form certified agent vapors by means of volumetric dilution by digital mass flow controllers. The diluted vapor is introduced into a flow cell housing the indicator samples. Fiber optic cables fitted with lenses launch and collect the light perpendicular to the films, in transmission mode, in order to monitor the intensity of light passing through the samples. FIG. 24 shows a schematic 2402 of the vapor generator, which generates DFP and CEES vapors. (MFC=mass flow controller).

The target analyte air flow passes over the sample, embedded in the film. The resulting color change is measured in real time with a white light source in which the light is passed perpendicularly through the sample. The light is then collected and carried into the receiving end of a commercially available Ocean Optics USB2000 UV/VIS spectrometer, where any color change is indicated by spectral absorption. The spectrometer is capable of 3 ms, real-time, continuous data acquisition, which enables us to measure response times with high precision. Fiber optic cables fitted with collimating lenses carry and collect the light guided through the sample. A bifurcated fiber optic bundle for transmitting the light from the light source to the sensor film, and recovering the optical changes of the sensor to the spectrometer, is used for testing surface coatings.

Validation of MIKE-Tape Operating Characteristics

In order to optimize and validate the operating conditions and characteristics for the MIKE-tape, a method was developed for quantifying the effects of temperature and humidity on sensitivity by means of a designed experiment (DOE) on film samples. Each film sample will be exposed either to a 1 µL droplet or to vapor phase at 50% IDLH concentration in a predetermined background environment for a length of time, after which its optical absorbance will be measured. The results of the experiment are analyzed with commercial Minitab® software to determine the response surface characteristics of the films. Thus, variations due to temperature and humidity are quantified. Measurements are taken under the conditions shown in the table in FIG. 25. Duplicate samples are measured to insure the quality of the data. These conditions were selected based on field relevance.

Evaluation of Long-Term Stability

To validate long term stability, the systems is tested under stress conditions to the improved sensor materials previously selected. Highly Accelerated Life Testing (HALT) is used to stress the sensors to failure in a relatively short time. HALT, however, does not determine the lifetime of the sensor, but it is an indicator for the relative stability of the elements being evaluated.

Stress Test 1: The sensor is stressed by being quickly cycled between hot (100□C) and wet (100% RH) conditions by exposing the sensor to boiling water vapor and relatively cool and dry conditions (ambient temperature and RH). This combination of conditions applies both temperature and humidity soaks and temperature and humidity shock cycles. If the sensor has an underlying weakness, this test is generally successful in stimulating failures in <100 hr. Sensor operation will be checked periodically throughout the test.

Stress Test 2: The sensor is stressed by being exposed to airborne contaminants at elevated concentrations. Building materials, especially carpets, caulking, paint, and particle board, have been found to emit volatile organic compounds (VOCS), and some buildings have been found to have levels of VOCs up to 400 times higher than outside. Sensors are exposed for one to four weeks to levels of the selected VOCs from 10-50 times higher than their typical levels. Sensor performance is checked periodically throughout the test.

MIKE-Tape Performance at ECBC and CUBRC Test Laboratories

Figure 29:
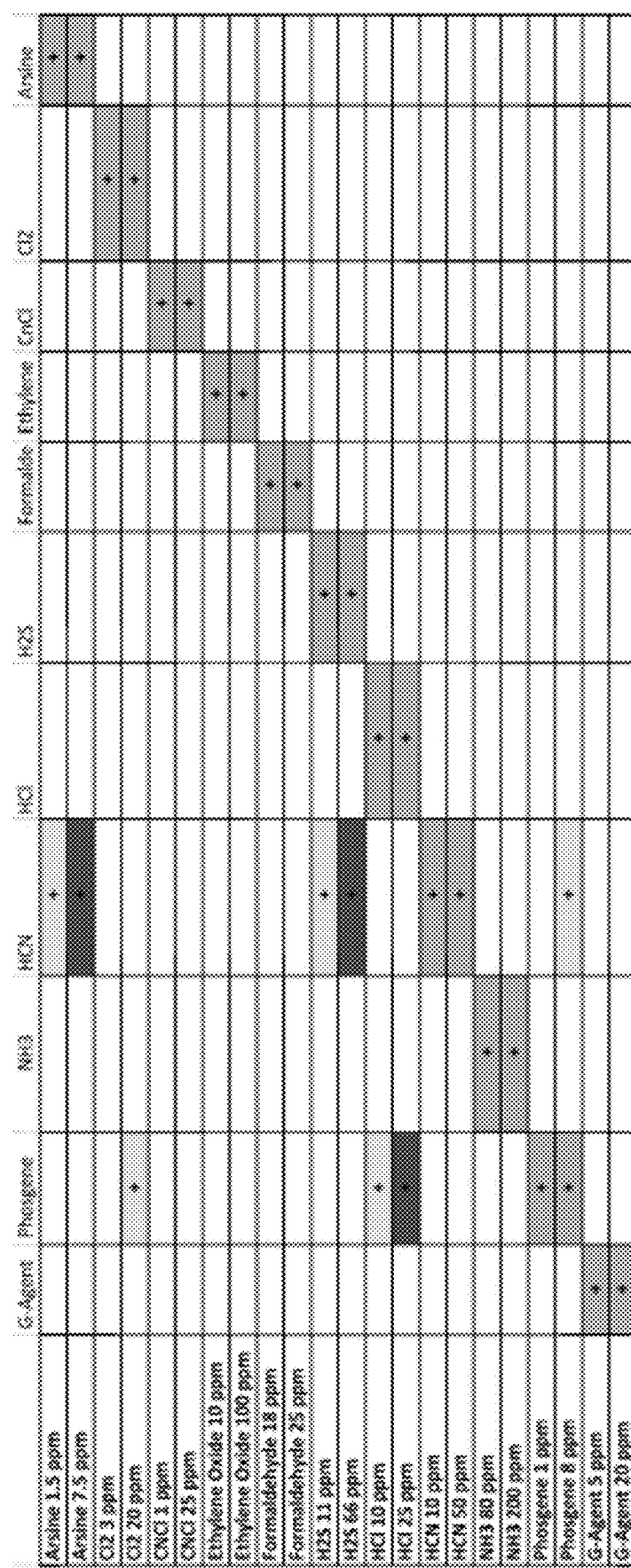
FIG. 29 shows a table of results of a very low level of cross reactivity among the sensor formulations.

To validate the described MIKE-tape systems and implementation, sensor coatings are fabricated and sent to ECBC laboratories for GB/GD, Vx and HD aerosol testing, while TIC sensor coatings are tested at CUBRC laboratories for testing against the target chemicals listed in the table in FIG. 29. Testing includes comprehensive environmental testing of CWA and TIC vapor sensor claddings to demonstrate the feasibility of coating functionality against a broad range of chemical contaminants under a range of temperature and humidity levels.

Calibration curve and sensitivity: Both simulant calibration data and live agent calibration data from previous development is used to evaluate the CWA Test System calibration and sensitivity parameters.

Precision: Repeated exposures of each sensor indicator to its target are conducted to measure precision and accuracy. A blind test is conducted in which the sensor signal is computed through its corresponding calibration curve. The resulting concentration are then be compared with the actual concentration levels.

Response time: Multiple exposures to varying concentrations of CWA vapors are conducted and compared with response time measurements from live agent testing.

Range: Calibration data will be used to determine the measurement dynamic range of each sensor element and evaluate the lower and upper detection limits.

Reproducibility: Repeated exposures to known levels of CWA simulant vapors, using at least three sensor arrays fabricated according to the same procedure, are conducted to evaluate the reproducibility of the sensing array.

CWAs such as V, H, and G agents and TIC vapors are detected in two ways:

a. Easy-to-use, simple, and rapid M8 test papers detect and differentiate among these agents. However, outdoors these test papers usually require frequent replacement because they are degraded by exposure to sun, dust, and rain. In addition, assessing their response requires visual inspection, and the indicators are limited to M8 paper matrix encapsulation; they cannot be coated onto other surfaces. Other spot test kits and detector tapes—such as the Chameleon Chemical Detection Armband sold by Morphix Technologies, and Draeger detector tubes—all share the same drawbacks.

b. Ionization mass spectrometry (IMS) systems, surface acoustic wave (SAW) electrochemical units, photoionization detectors (PIDs), and other popular point detectors for chemicals and CWAs all require trained personal to operate and calibrate them. Finally, open path spectroscopy units (stand-off detectors) can also detect multiple compounds, but they are very bulky and expensive, and like all others mentioned require trained operators and frequent maintenance.

Neither category of detectors is suitable for integration into drone copters because of their size, weight, hardware, and software interface requirements. The disclosed approach bridges the gap between simple colorimetry and passive integration into drones, by applying customized, selective, sensitive, and reliable colorimetric claddings onto the copter camera. The sensor claddings will detect multiple CWAs and TICs, in both aerosol and vapor phase, under a full range of real-world environmental conditions.

Sensor Array for TIC Colorimetric Detection

In previous work, a handheld vapor detection system was developed based on developed sensor claddings for measuring multiple toxic industrial chemicals (TICs). Some of the developed TIC sensor arrays 2601 are shown in FIG. 26 with their target detection specifications 2602.

Figure 27:
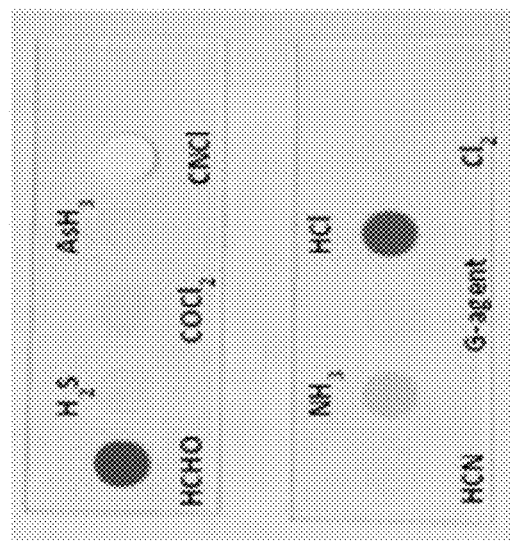
FIG. 27 shows the previously developed results for chemical sensor array and recorded measurement ranges of the device.

Samples of HCN and $H_2S$ sensor chemistries were tested against 25 ppm HCN and 50 ppm $H_2S$ in vapor phase, showing strong reactivity with an intensely visualized color change (FIG. 27). Indicators were immobilized in UV-curable silicon. Shown in FIG. 27 is the visual observation of color change of developed colorimetric indicators immobilized in proprietary polymers. FIG. 27 2701 (left) shows the result of $H_2S$ colorimetric chemistry tested with 50 ppm $H_2S$ vapor; and shown in FIG. 27 2702 (right) is the result of HCN sensor chemistry tested with 25 ppm HCN vapor.

Figure 28:
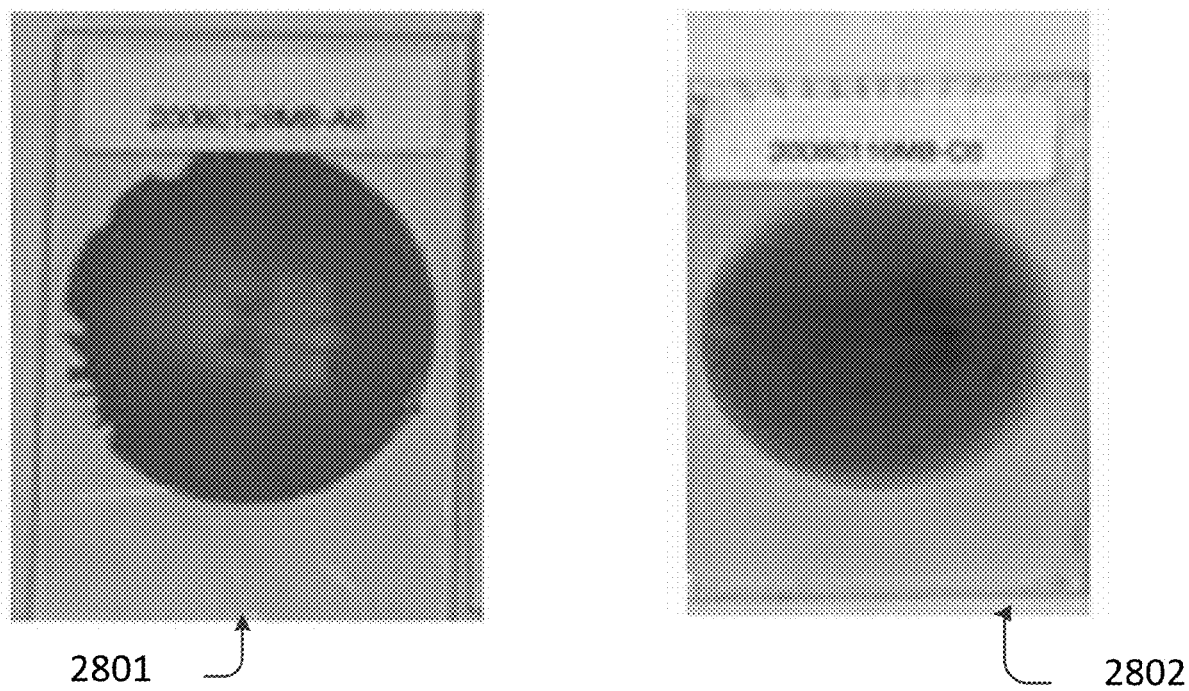
FIG. 28 shows the result of H$_2$S and HCN colorimetric chemistry testing.

Unlike other colorimetric sensor arrays, with reported high degrees of cross-response, the developed MIKE-tape colorimetric coatings are selected for the highest degree of selectivity towards their target chemicals. The table in FIG. 28 shows results of a very low level of cross reactivity among the sensor formulations, enabling it to selectively identify the level of each TIC.

Figure 30A:
FIG. 30A-C show images of a test implementation of MIKE-tape for detecting chlorine gas.
Figure 30B:

Developed colorimetric optical claddings are tested against water immersion for implementation as armband chemical warfare agent colorimetric sensor for military use. Validation results shown in FIG. 29 of exposed film substrates after submersion in tap water 2901 (top) and salt water (bottom) 2902 for 0, 5, 15, 30, and 60 min. FIGS. 30A and 30B show photographs of the sensor cladding response to 10 ppm chlorine vapor after submersion in tap water and salt water. The photos show that described polymer colorimetric indicator cladding was unaffected by immersion for up to an hour in either tap water or salt water.

To provide a rapid and effective response to chemical release, first responders need a reliable, portable, and rugged device that identifies and characterizes multiple chemical hazards in rapidly-evolving emergency situations. Addressing such a need is the developed "MOSA"—a Multi-Analyte Optical Sensor Array whose underlying technology consists of optical indicator-based chemical sensors arranged in a miniaturized multiple parallel waveguide array. Each individual waveguide element is chemically sensitive to its target chemical agent. A compact, inexpensive, optoelectronic system measures the presence and concentration of analytes that the waveguide encounters by monitoring the intensity of the light carried by the optical waveguides.

Transparent MIKE-Tape Visual Testing

Operational capability and performance of MIKE-take indicators and polymer substrates were tested for system validation using a typical UAS/UGS camera system with affixed with MIKE-tape and individual indicators. These tests were utilized to validate performance during operation and to identify solutions to improve operation performance. Depth of field utility of the camera was demonstrated through these validation tests.

Figure 30C:
Figure 31A:
Figure 31B:
Figure 32C:
FIG. 32A-C show images of a test implementation of MIKE-tape for detecting ammonia.
Figure 32A:
Figure 32B:
Figure 32C:
Figure 33A:
FIG. 33A-C show images of a test implementation of MIKE-tape for detecting cyanide gas (HCN).
Figure 33B:
Figure 33C:

FIG. 30A-C show still images taken from the implemented system camera with MIKE-tape affixed to the camera during testing for chlorine gas exposure at 20 ppm for 0 seconds (FIG. 30A), 15 seconds (FIG. 30B) and 30 seconds (FIG. 30C) with the applicable indicator cladding. FIG. 31A-C show still images taken from the implemented system camera with MIKE-tape affixed to the camera during testing for phosgene vapor exposure at concentrations of 25 ppm for 0 seconds (FIG. 31A), 30 seconds (FIG. 31B) and 60 seconds (FIG. 31C) with the applicable indicator cladding. FIG. 32A-C show still images taken from the implemented system camera with MIKE-tape affixed to the camera during testing for ammonia exposure at a concentration of 200 ppm for 0 seconds (FIG. 32A), 30 seconds (FIG. 32B) and 60 seconds (FIG. 32C) with the applicable indicator cladding. FIG. 33A-C show still images taken from the implemented system camera with MIKE-tape affixed to the camera during testing for cyanide gas exposure at a concentration of 55 ppm for 0 seconds (FIG. 33A), 30 seconds (FIG. 33B) and 60 seconds (FIG. 33C) with the applicable indicator cladding.

In an alternative embodiment, one or more MIKE-tape indicator spots clad to the substrate have one half of the indicator spot exposed to the environment, and the other half of the spot covered, or sealed from the environment. This implementation allows a simpler and more reliable visual detection of indicator colorimetric changes, particularly when viewed against changing background conditions which would be present during real-world operation of a UAS or UGS implementation of MIKE-tape. This embodiment also provides a more reliable system for autonomous detection by an optoelectronic system or image processing.

Figure 34A:
FIG. 34A-C show images of a test implementation of MIKE-tape for detecting chlorine gas with a half-tape sensor.
Figure 34B:
Figure 34C:

FIG. 34A-C show still images taken from the implemented system camera with MIKE-tape affixed to the camera during testing for chlorine gas exposure with a split indicator at concentrations of 20 ppm for 0 seconds (FIG. 34A), 15 seconds (FIG. 34B) and 30 seconds (FIG. 34C) with the applicable indicator cladding.

The MIKE-tape system exhibits broad spectrum chemical, biological, explosives, and toxic industrial chemical detection, with passive integration that does not require the readout device or sophisticated data processing of other colorimetric dot array sensors.

There is a strong military need for a rugged, reliable means of chemical detection that will be easy to integrate into unmanned autonomous systems (UAS). There is an even greater need for an automated system that eliminates the human from the liquid CWA detection loop while maintaining the accuracy of detection. Many embodiment applications of MIKE-Tape may meet this need including the exemplar embodiment of where the MIKE-tape is integrated into drone copters through the adhesion of a functionalized and highly developed colorimetric chemical sensor tape onto the copter camera lens.

What has been described herein is considered merely illustrative of the principles of this invention. Accordingly, it is well within the purview of one skilled in the art to provide other and different embodiments within the spirit and scope of the invention.

What is claimed is:

1. A system for the passive detection of target airborne toxins in an environment, comprising:
    at least one colorimetric indicator which changes color when exposed to at least one airborne toxin;
    a transparent polymer substrate, wherein the transparent polymer substrate is an optical grade, wherein the at least one colorimetric indicator is clad and immobilized to the transparent polymer substrate;
    a transparent window or lens;
    an optical detector located adjacent to a non-environment facing surface of the transparent window or lens;
    wherein the at least one airborne toxin is chemical warfare agent or a toxic industrial chemical;
    wherein the transparent polymer substrate is a cross-linked combination of a primary polymer and a chemically inert co-polymer silicon backbone;

wherein the primary polymer is a urethane acrylate polymer;

wherein the transparent polymer substrate is affixed to an environment facing surface of the transparent window or lens and the transparent polymer substrate is positioned between the optical detector and the environment such that a line of sight from the environment and the optical detector passes through the transparent polymer substrate;

whereby when exposed to a target airborne toxin the corresponding colorimetric indicator clad to the transparent polymer substrate changes color, indicating presence of the at least one target airborne toxin by detecting color changes by the optical detector.

2. The system of claim 1 wherein the airborne toxin is a chemical warfare agent chosen from the group consisting of: a nerve agent, a blister agent, a blood agent.

3. The system of claim 1 wherein the at least one airborne toxin is a chemical warfare agent chosen from the group consisting of: sarin gas, soman gas, vx gas, chlorine gas, phosgene vapor, chlorine gas, cyanide gas.

4. The system of claim 1 wherein the at least one airborne toxin is sarin gas or soman gas.

5. The system of claim 4 wherein the colorimetric indicator comprises an indicator dye complexed with a metal salt.

6. The system of claim 1 wherein the colorimetric indicator comprises an indicator dye complexed with a metal salt mixed with a hydrolyzing agent.

7. The system of claim 1 wherein the polymer substrate is treated with a free volume enhancer additive.

8. The system of claim 7 wherein the free volume enhancer additive is a poly-styrene-sulfonate derivate.

9. The system of claim 8 wherein the poly-styrene-sulfonate derivate is poly-styrene-sulfonate-trisilanol-isooctyl substituted.

10. The system of claim 1 wherein the polymer substrate is transparent.

11. The system of claim 1 wherein polymer substrate is affixed with an adhesive backing.

12. A method for passively detecting target airborne toxins comprising:

exposing to an environment at least one colorimetric indicator which changes color when exposed to at least one airborne toxin in the environment;

wherein the at least one colorimetric indicator is immobilized into a transparent polymer substrate;

wherein the transparent polymer substrate is an optical grade, wherein the at least one airborne toxin is chemical warfare agent or a toxic industrial chemical;

wherein the transparent polymer substrate is a cross-linked combination of a primary polymer and a chemically inert co-polymer silicon backbone;

wherein the primary polymer is a urethane acrylate polymer;

wherein the at least one colorimetric indicator is cross-linked to the transparent polymer substrate and cured with the transparent polymer substrate by exposure to ultraviolet light and heat;

wherein the transparent polymer substrate is affixed to an environment facing surface of the transparent window or lens and the transparent polymer substrate is positioned between an optical detector and the environment such that a line of sight from the environment to the optical detector, passes through the at least one colorimetric indicator;

discerning color changes to the transparent polymer substrate by the optical detector, indicating presence of the target airborne toxin.

13. The method of claim 12 wherein the airborne toxin is a chemical warfare agent chosen from the group consisting of: a nerve agent, a blister agent, a blood agent.

14. The method of claim 12 wherein the at least one airborne toxin is a chemical warfare agent chosen from the group consisting of: sarin gas, soman gas, vx gas, chlorine gas, phosgene vapor, chlorine gas, cyanide gas.

15. The method of claim 12 wherein the at least one airborne toxin is sarin gas or soman gas.

16. The method of claim 14 wherein the colorimetric indicator comprises an indicator dye complexed with a metal salt.

17. The method of claim 12 wherein the colorimetric indicator comprises an indicator dye complexed with a metal salt mixed with a hydrolyzing agent.

18. The method of claim 12 wherein transparent polymer substrate is treated with a free volume enhancer additive.

19. The method of claim 18 wherein the free volume enhancer additive is a poly-styrene-sulfonate derivate.

20. The system of claim 19 wherein the poly-styrene-sulfonate derivate is poly-styrene-sulfonate-trisilanol-isooctyl substituted.

21. The method of claim 12 wherein polymer substrate is affixed with an adhesive backing.

* * * * *